US010752946B2

United States Patent
Chu et al.

(10) Patent No.: US 10,752,946 B2
(45) Date of Patent: Aug. 25, 2020

(54) METHODS AND COMPOSITIONS FOR ENRICHMENT OF TARGET POLYNUCLEOTIDES

(71) Applicant: MYRIAD WOMEN'S HEALTH, INC., South San Francisco, CA (US)

(72) Inventors: Clement S. Chu, San Francisco, CA (US); Noah C. Welker, Half Moon Bay, CA (US); Henry H. Lai, San Francisco, CA (US)

(73) Assignee: MYRIAD WOMEN'S HEALTH, INC., South San Francisco, CA (US)

( * ) Notice: Subject to any disclaimer, the term of this patent is extended or adjusted under 35 U.S.C. 154(b) by 30 days.

(21) Appl. No.: 15/873,687

(22) Filed: Jan. 17, 2018

(65) Prior Publication Data
US 2018/0216176 A1    Aug. 2, 2018

Related U.S. Application Data

(60) Provisional application No. 62/452,848, filed on Jan. 31, 2017.

(51) Int. Cl.
C12Q 1/6869 (2018.01)
C12N 15/10 (2006.01)
(Continued)

(52) U.S. Cl.
CPC .......... *C12Q 1/6869* (2013.01); *C12N 9/93* (2013.01); *C12N 15/1031* (2013.01);
(Continued)

(58) Field of Classification Search
None
See application file for complete search history.

(56) References Cited

U.S. PATENT DOCUMENTS 5,476,930 A    12/1995 Letsinger et al.
5,780,613 A    7/1998 Letsinger et al.
(Continued)

FOREIGN PATENT DOCUMENTS

WO    WO2010/151842 A2    12/2010
WO    WO2012003374 A2    1/2012
(Continued)

OTHER PUBLICATIONS

Gundmundsson, J., et al., Genome-wide association and replication studies identify four variants associated with prostate cancer susceptibility, Nat Genet 41:1122-1126, 2009.
(Continued)

*Primary Examiner* — Kaijiang Zhang
(74) *Attorney, Agent, or Firm* — FisherBroyles, LLP; Jill A. Jacobson; Victoria Brewster

(57) ABSTRACT

High-fidelity, high-throughput nucleic acid sequencing enables healthcare practitioners and patients to gain insight into genetic variants and potential health risks. However, previous methods of nucleic acid sequencing often introduce sequencing errors (for example, mutations that arise during the preparation of a nucleic acid library, during amplification, or sequencing). Provided herein are methods and compositions for sequencing nucleic acids. Further provided are methods of identifying an error in a nucleic acid sequence.

39 Claims, 9 Drawing Sheets
Specification includes a Sequence Listing.

(51) Int. Cl.
*C12Q 1/6809* (2018.01)
*C12Q 1/686* (2018.01)
*C12N 9/00* (2006.01)

(52) U.S. Cl.
CPC ........... *C12Q 1/686* (2013.01); *C12Q 1/6809* (2013.01); *C12Q 2600/156* (2013.01)

(56) References Cited

U.S. PATENT DOCUMENTS

| | | | |
|---|---|---|---|
| 7,115,400 | B1 | 10/2006 | Adessi et al. |
| 8,383,338 | B2 | 2/2013 | Kitzman et al. |
| 9,092,401 | B2 | 7/2015 | Richards et al. |
| 9,309,556 | B2 | 4/2016 | Myllykangas et al. |
| 2008/0160580 | A1 | 7/2008 | Adessi et al. |
| 2008/0286795 | A1 | 11/2008 | Kawashima et al. |
| 2010/0022406 | A1 | 1/2010 | Srinivasan et al. |
| 2012/0295819 | A1 | 11/2012 | Leamon et al. |
| 2013/0171185 | A1 | 7/2013 | Settembre et al. |
| 2014/0024536 | A1* | 1/2014 | Richards et al. ..... C12Q 1/6874 506/2 |
| 2014/0024541 | A1 | 1/2014 | Richards et al. |
| 2014/0121116 | A1 | 5/2014 | Richards et al. |
| 2014/0141982 | A1 | 5/2014 | Jacobson et al. |
| 2014/0162278 | A1 | 6/2014 | Richards et al. |
| 2014/0274740 | A1* | 9/2014 | Srinivasan et al. .. C12Q 1/6806 506/2 |
| 2015/0017635 | A1 | 1/2015 | Myllykangas et al. |
| 2015/0044687 | A1* | 2/2015 | Schmitt et al. ....... C12Q 1/6869 435/6.12 |
| 2015/0205914 | A1 | 7/2015 | Richards et al. |
| 2015/0284712 | A1 | 8/2015 | Kurihara et al. |
| 2015/0275289 | A1 | 10/2015 | Otwinowski et al. |
| 2015/0353926 | A1 | 12/2015 | Rigatti et al. |
| 2016/0068903 | A1 | 3/2016 | Zhou et al. |
| 2016/0115544 | A1 | 4/2016 | Elzinga et al. |
| 2017/0321270 | A1 | 11/2017 | Haque et al. |
| 2017/0355984 | A1 | 12/2017 | Evans et al. |
| 2018/0089364 | A1 | 3/2018 | Muzzey et al. |
| 2018/0201994 | A1 | 7/2018 | Beauchamp et al. |
| 2018/0216103 | A1 | 8/2018 | Lai et al. |

FOREIGN PATENT DOCUMENTS

| | | |
|---|---|---|
| WO | WO2012040387 A1 | 3/2012 |
| WO | WO2013112923 A1 | 8/2013 |
| WO | WO2016/010856 A1 | 1/2016 |
| WO | WO2016130704 A2 | 8/2016 |
| WO | WO2018144217 A1 | 8/2018 |
| WO | 2018/161019 A1 | 9/2018 |

OTHER PUBLICATIONS

Illumina, Quality Scores for Next Generation Sequencing, Pub. No. 770-2011-030, Oct. 31, 2011.
Illumina, Understanding Illumina Quality Scores, Pub. No. 770-2012-058, Apr. 23, 2014.
Illumina, Calculating Percent Passing Filter for Patterned and Nonpatterned Flow Cells, Pub. No. 770-2014-043-B, 2017.
Samorodnitsky, E., et al., Comparison of custom capture for targeted next-generation DNA sequencing, J Mol Diagn 17:64-75, Jan. 15, 2015.
Turner, E., et al., Massively parallel exon capture and library-free resequencing across 16 genomes, Nat. Methods 6:315-316, 2009.
Horhota, A.T., et al., Glycerol Nucleoside Triphosphates: Synthesis and Polymerase Substrate Activities, 2006, Org. Lett. 8(23):5345-5347.
Altschul, S.F., et al., Basic Local Alignment Search Tool, 1990, J. Mol. Biol. 215:403-410.
Henikoff, S., et al., Amino acid substitution matrices from protein blocks, 1992, Proc. Natl. Acad. Sci. 89:10915-10919.
Karlin, S., et al., Applications and statistics for multiple high-scoring segments in molecular sequences, 1993, Proc. Natl. Acad. Sci. 90:5873-5877.
Higgins, D.G., et al., CLUSTAL: a package for performing multiple sequence alignment on a microcomputer, 1988, Gene 73:237-244.
Pearson, W.R., et al., Improved tools for biological sequence comparison, 1988, Proc. Natl. Acad. Sci. 85:2444-2448.
Alnemri, E.S., et al., Activation of Internucleosomal DNA Cleavage in Human CEM Lymphocytes by Glucocorticoid and Novobiocin, 1990, J. Biol. Chem. 205(28):17323-17333.
Richards, O.C., et al., Chemical Mechanism of Sonic, Acid, Alkaline and Enzymic Degradation of DNA, 1965, J. Mol. Biol. 11:327-340.
Ahn, J., et al., Asymmetrical barcode adapter assisted recovery of duplicate reads and error correction strategy to detect rare mutations in circulating tumor DNA, May 2, 2017, Nature 7(46678):1-9.
NimbleGen Seq EZ Library SR User's Guide, Roche, 2014.
Hybridization capture of DNA libraries using xGen Lockdown Probes and Reagents, IDT Integrated DNA Technologies, 2015.
Zhong, S., et al., High-Throughput Illumina Strand-Specific RNA Sequencing Library Preparation, Cold Spring Harb Protoc 2011(8):940-949, 2011.
Hopmans, E., A programmable method for massively parallel targeted sequencing, Nucleic Acids Research 42(10): e88, pp. 1-16, Apr. 29, 2014.
Mertes, F., et al., Targeted Enrichment of Genomic DNA Regions for Next-Generation Sequencing, Briefings in Functional Genomics 10(6):374-386.
Myllykangas, S., et al., Efficient Targeted Resequencing of Human Germline and Cancer Genomes by Oligonucleotide-Selective Sequencing, Nat Biotechnol 29(11):1024-1027, Oct. 23, 2011.
Ng, S.B., et al. Targeted Capture and Massively Parallel Sequencing of Twelve Human Exomes, Nature 461 (7261):272-276.

\* cited by examiner

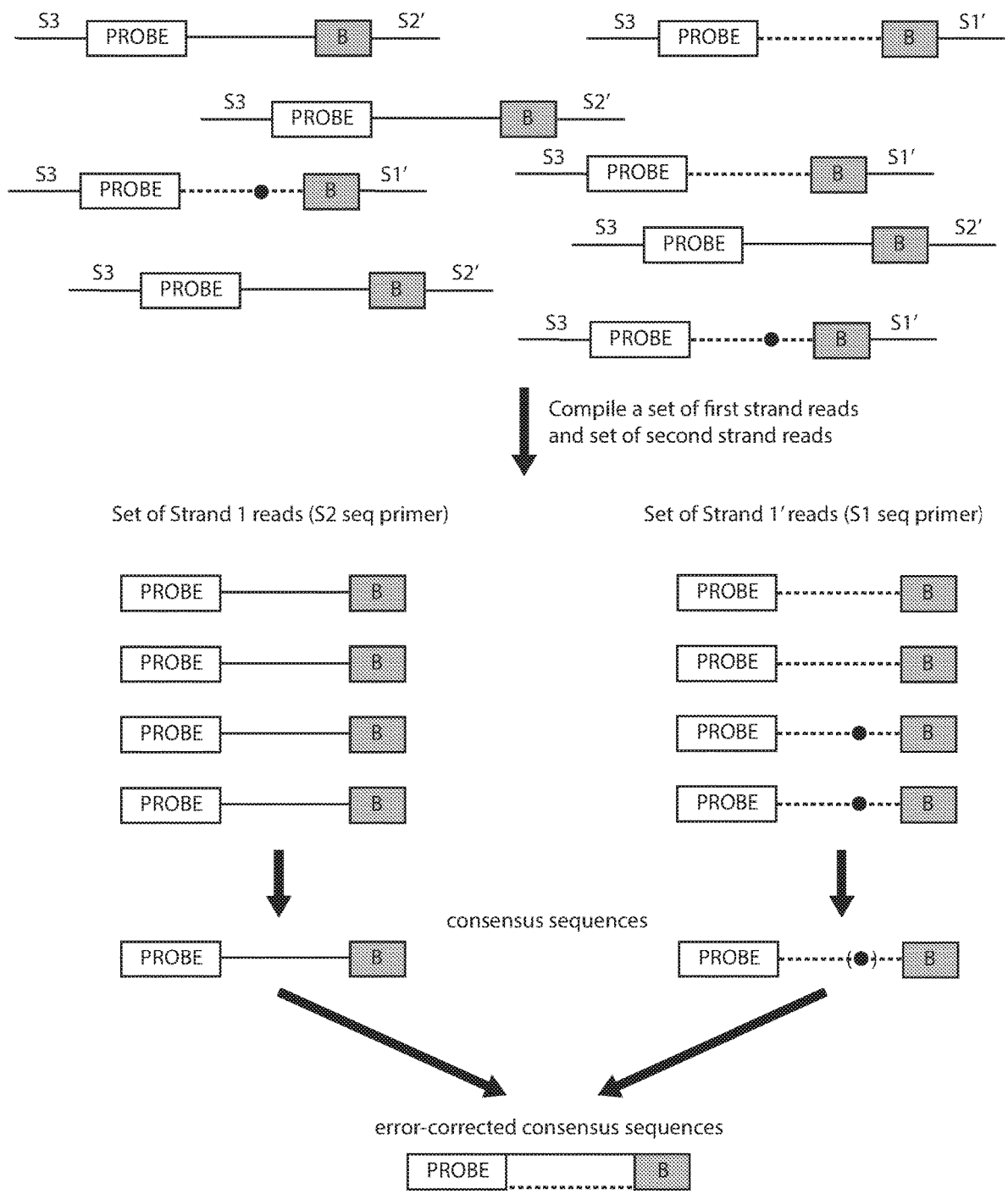

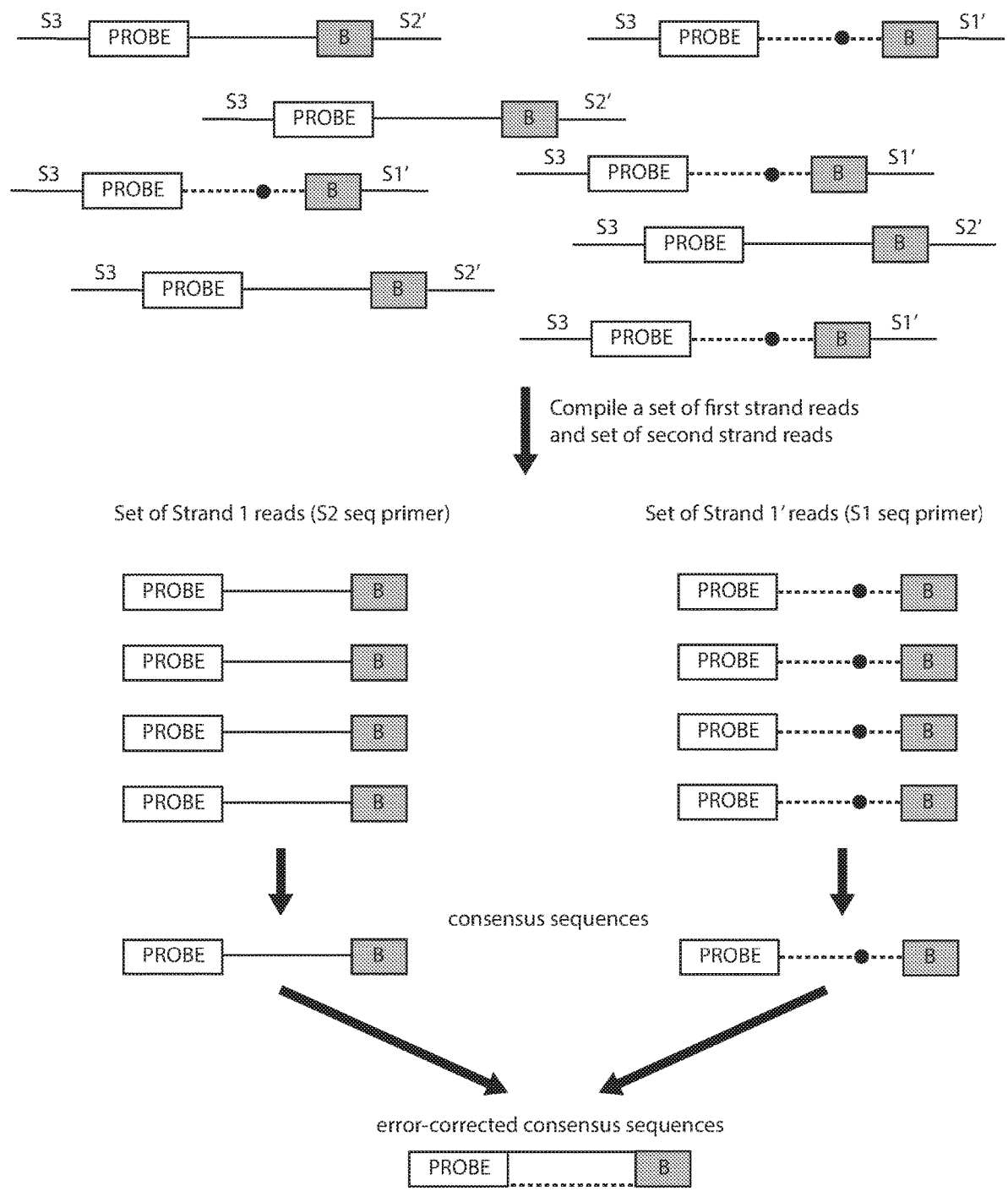

SEQUENCE LISTING

<160> NUMBER OF SEQ ID NOS: 11

<210> SEQ ID NO 1
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
catcgagcta tgat                                                         14

<210> SEQ ID NO 2
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
acacgctacg atgt                                                         14

<210> SEQ ID NO 3
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
cactcagcag cacgacgatc acagatgtgt ataagagaca gt                          42

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
actgtgtaaa acgacggcca gt                                                22

```
<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 5
cagacgtgtg ctcttccgat ct                                               22

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
caagcagaag acggcatacg agat                                             24

<210> SEQ ID NO 7
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
aatgatacgg cgaccaccga gatctacac                                        29

<210> SEQ ID NO 8
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
aatgatacgg cgaccaccga gatctacac                                        29

<210> SEQ ID NO 9
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gtgactggag ttcagacgtg tgctcttccg atct                                  34

<210> SEQ ID NO 10
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
taatacgact cactataggg actggccgtc gttttacaca gt                         42

<210> SEQ ID NO 11
```

```
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
cactcagcag cacgacgatc acagatgtgt ataagagaca gt                         42
```

METHODS AND COMPOSITIONS FOR ENRICHMENT OF TARGET POLYNUCLEOTIDES

CROSS-REFERENCE TO RELATED APPLICATIONS

This application claims the benefit of U.S. Provisional Application No. 62/452,848, filed on Jan. 31, 2017, which is incorporated herein by reference in its entirety.

SEQUENCE LISTING

The instant application contains a Sequence Listing which has been submitted electronically in ASCII format and is hereby incorporated by reference in its entirety. Said ASCII copy, created on Feb. 13, 2018, is named 04268_046US1_SL.txt and is 2,797 bytes in size.

FIELD OF THE INVENTION

The present invention relates to methods and compositions for sequencing nucleic acids.

BACKGROUND

Next-generation sequencing (NGS) allows small-scale, inexpensive genome sequencing with a turnaround time measured in days. However, as NGS is generally performed and understood, all regions are sequenced with roughly equal probability, meaning that a large amount of genomic sequence is collected and discarded to collect sequence information from the relatively low percentage of areas where function is understood well enough to interpret potential mutations. Generally, purifying from a full-genome sample only those regions one is interested in is conducted as a separate step from sequencing. It is usually a days-long, low efficiency process in the current state of the art.

Next generation sequencing of nucleic acids has greatly increased the rate of genomic sequencing, thereby bringing in a new era for medical diagnostics, forensics, metagenomics, and many other applications. However, these high-throughput approaches often incorporate sequence errors, resulting in inaccuracies in a constructed consensus sequence. These errors can arise, for example, during nucleic acid amplification or sequencing, or downstream analysis. Additionally, errors can arise due to chemical damage of the original nucleic acid molecule. In some cases, as many as 1% of sequenced bases can be incorrectly identified. These errors in the nucleic acid consensus sequence limit the reliability of known NGS methods.

Direct Targeted Sequencing (DTS) is a modification to the standard sequencing protocol employed by Illumina, Inc. that allows the sequencing substrate (i.e., the flow cell) to become a genomic sequence capture substrate as well. Without adding another instrument to the normal flow of a typical NGS protocol, the DTS protocol modifies the sequencing surface to capture genomic DNA (gDNA) from a specially prepared library. The captured library is then sequenced as a normal gDNA library would be. However, modification of the sequencing substrate and accompanying library preparation according to previous suggestions result in inefficiencies, reduced reliability and reproducibility, and waste valuable sample. Improvements to the DTS process are therefore desirable.

BRIEF SUMMARY OF THE INVENTION

Methods and compositions are provided for preparing and sequencing target nucleic acids.

In one aspect, methods are provided for preparing a target nucleic acid duplex molecule for sequencing. In some embodiments, the methods include:

(a) ligating an adaptor to each end of a target nucleic acid duplex that includes first and second nucleic acid strands that are complementary to one another, wherein each of the adaptors includes: (i) a double stranded region that includes a molecular barcode; and (ii) first and second single stranded regions, wherein the first single stranded region and optionally, a portion of the double stranded region, of each of the adaptors includes a sequence S1 that is 5' of the molecular barcode sequence and the second single stranded region and optionally, a portion of the double stranded region, of each adaptor includes a sequence S2' that is 3' of the molecular barcode sequence, wherein sequences S1 and S2' are different;

(b) amplifying the ligated nucleic acids produced in (a) using primers with sequence S1 and the complement of S2', thereby producing: (i) amplified copies of the first strand that include sequence S1 at the 5' end and a first molecular barcode sequence A between S1 and the target nucleic acid sequence of the first strand, and sequence S2' at the 3' end and a second molecular barcode sequence B between S2' and the target nucleic acid sequence of the first strand; (ii) amplified copies of the second strand that include sequence S1 at the 5' end and the complement B' of the second molecular barcode sequence between S1 and the target nucleic acid sequence of the second strand, and sequence S2' at the 3' end and the complement A' of the first molecular barcode sequence between S2' and the target nucleic acid sequence of the second strand; and amplified complements of (i) and (ii);

(c) hybridizing and extending a primer that includes: (i) a probe sequence that is complementary to a portion of the target nucleic acid sequence of the first and/or second strand, and (ii) a sequence S3, thereby producing primer extension products complementary to the second strand that include S3 at the 5' end and either S1' or S2' at the 3' end and that include molecular barcode sequence B between the target nucleic acid sequence and S1' or S2', and/or primer extension products complementary to the first strand that include S3 at the 5' end and either S1' or S2' at the 3' end and that include molecular barcode sequence A' between the target nucleic acid sequence and S1' or S2';

(d) differentially amplifying the primer extension products in first and second reactions (e.g., in temporally or spatially separated first and second reactions), wherein a first reaction includes amplification using a first primer that includes a sequence complementary to S3 and optionally, one or more sample index sequence(s), and a second primer that includes S2 and one or more sample index sequence(s), and wherein a second reaction includes amplification using a first primer that includes a sequence complementary to S3 and optionally, one or more sample index sequence(s), and a second primer that includes S1 and one or more sample index sequence(s), thereby producing amplified primer extension products for sequencing.

In some embodiments, the target nucleic acid duplex includes cell-free DNA, for example, cell-free tumor DNA or cell-free fetal DNA. In some embodiments, the target nucleic acid duplex is enriched from a nucleic acid library. In some embodiments, the target nucleic acid duplex is enriched using a set of capture probes for a region of interest.

In some embodiments, the adaptors are Y-shaped, and the first and second single stranded regions are on separate polynucleotides. In other embodiments, the adaptors are U-shaped, and the first and second single stranded regions are on the same polynucleotide. In some embodiments, the adaptors include a combination of both Y-shaped and U-shaped adaptors.

In some embodiments, the molecular barcode sequences A and B are the same. In other embodiments, the molecular barcode sequences A and B are different. In some embodiments, the molecular barcode sequences are about 4 to about 15, or about 12 to about 15 nucleotides in length.

In some embodiments, amplifying the adaptor ligated target nucleic acid duplex molecules (e.g., in step (b)) includes polymerase chain reaction (PCR) or a linear amplification method.

In some embodiments, the step of hybridizing and extending a primer (e.g., step (c)) includes inclusion of blocking oligonucleotides that include sequences S1 and S2, and that each include a modification at the 3' end to prevent extension by a polymerase.

In some embodiments, the step of hybridizing and extending a primer (e.g., step (c)) can be performed (e.g., repeated) with a plurality of different probes, in the same or different reaction mixtures, to produce a plurality of primer extension products that will provide different start points for sequencing of the target nucleic acid sequence.

In some embodiments, the sample index sequences, if any, in the first and second primers (e.g., in step (d)) are the same. In other embodiments, the sample index sequences, if any, in the first and second primers are different. In some embodiments, the method further includes combining the primer extension products produced in separate amplification reactions (e.g., in step (d)), prior to sequencing.

In some embodiments, amplifying the primer extension products (e.g., in step (d) includes PCR or a linear amplification method.

In another aspect, methods are provided for sequencing a target nucleic acid, including preparing a target nucleic acid duplex for sequencing according to the methods disclosed herein, and sequencing amplified primer extension products thereby produced (e.g., in step (d)). In some embodiments, the method includes combining the primer extension products produced in separate amplification reactions (e.g., in step (d)), prior to sequencing.

In some embodiments, the method includes performing a first read of a first strand of the target sequence, including sequencing with first primers that include sequence S1 and second primers that include sequence S2, in the same or different reaction mixtures. In some embodiments, the first read with one of the primers begins 5' of the molecular barcode sequence and the first read with the other primer begins at the molecular barcode sequence. In some embodiments, the first read with both of the primers begins 5' of the molecular barcode sequence. In some embodiments, the first read begins at the terminus or within a sample index sequence.

In some embodiments, second reads are performed to read sample index sequence(s).

In some embodiments, a set of first reads is performed to construct a consensus sequence of the first strand of the target nucleic acid duplex. In some embodiments, the set of first strand reads is compiled based on sequence distance or alignment to a reference sequence.

In some embodiments, constructing the first strand consensus sequence includes: comparing the first strand reads in the set of first strand reads; identifying and removing errors in the set of first strand reads; and constructing an error-corrected first strand consensus sequence. In some embodiments, one or more mutation is identified by comparison of the error-corrected consensus sequence to a reference sequence. In some embodiments, the method further includes sequencing the second strand of the target nucleic acid duplex and constructing a consensus sequence of the second strand of the target nucleic acid duplex. For example, the method may include: comparing the first strand consensus sequence and the second strand consensus sequence; identifying and removing errors in the set of first strand reads and the set of second strand reads; and constructing an error-corrected duplex consensus sequence. In some embodiments, one or more chemical lesion or error introduced in a step of a method as described herein (e.g., sequencer error; polymerase error during PCR) may be identified by comparison of the sequences of the two strands in the error-corrected duplex consensus sequence. In some embodiments, the method includes distinguishing between a chemical lesion or introduced error and a mutation by comparison of the sequences of the two strands in the error-corrected duplex consensus sequence, wherein an error present in only one strand indicates a chemical lesion. In some embodiments, an error on both strands indicates a mutation.

In another aspect, a method is provided for preparing a nucleic acid sequencing library, including preparing a plurality of target DNA duplexes for sequencing in a method described herein.

In another aspect, a nucleic acid sequencing library is provided that includes a plurality of amplified primer extension products prepared according to a method described herein.

BRIEF DESCRIPTION OF THE DRAWINGS

FIG. 7B illustrates an exemplary method of compiling of set of first strand reads and a set of second strand reads, wherein the first strand and the second strand are complementary strands from the same parent duplex nucleic acid molecule. Errors could have arisen in Strand 1', for example, during amplification.

FIG. 7C illustrates another exemplary method of compiling of set of first strand reads and a set of second strand reads, wherein the first strand and the second strand are complementary strands from the same parent duplex nucleic acid molecule. Errors could have arisen in Strand 1', for example, prior to amplification, such as by chemical damage to the nucleic acid strand.

DETAILED DESCRIPTION

Figure 1A:
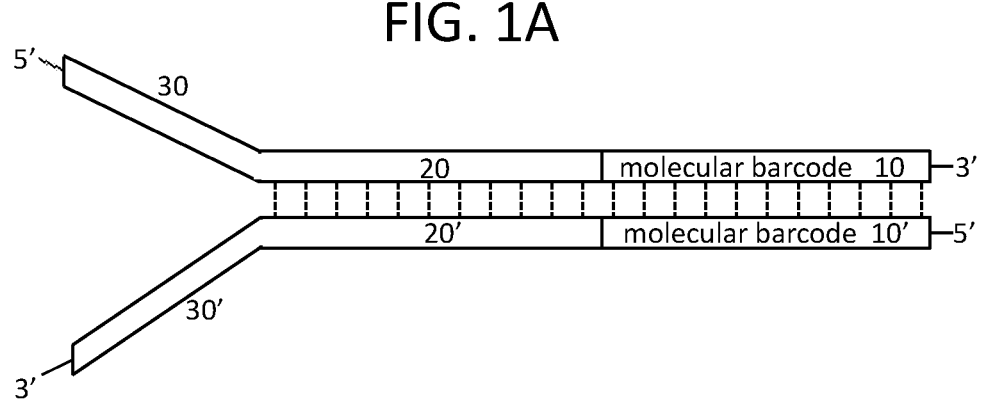
FIG. 1A illustrates one example of a Y-shaped sequencing adapter comprising a duplex molecular barcode.

The invention provides compositions and methods for preparing and sequencing nucleic acids. Among the advantages of the methods described herein are specificity of the position in which sequencing begins and control over the amount of nucleic acid to be sequenced. The methods described herein have reduced complexity in comparison to other sequencing methods, including the presence of only one molecular barcode on the nucleic acid construct that is sequenced. Further, the methods provide a sequencing start position that may be manipulated to provide an enhanced amount of information.

Unless defined otherwise herein, all technical and scientific terms used herein have the same meaning as commonly understood by one of ordinary skill in the art to which this invention belongs. Singleton, et al., *Dictionary of Microbiology and Molecular Biology*, second ed., John Wiley and Sons, New York (1994), and Hale & Markham, *The Harper Collins Dictionary of Biology*, Harper Perennial, N.Y. (1991) provide one of skill with a general dictionary of many of the terms used in this invention. Any methods and materials similar or equivalent to those described herein can be used in the practice or testing of the present invention.

The practice of the present invention will employ, unless otherwise indicated, conventional techniques of molecular biology (including recombinant techniques), microbiology, cell biology, and biochemistry, which are within the skill of the art. Such techniques are explained fully in the literature, for example, *Molecular Cloning: A Laboratory Manual*, second edition (Sambrook et al., 1989); *Oligonucleotide Synthesis* (M. J. Gait, ed., 1984; *Current Protocols in Molecular Biology* (F. M. Ausubel et al., eds., 1994); *PCR: The Polymerase Chain Reaction* (Mullis et al., eds., 1994); and *Gene Transfer and Expression: A Laboratory Manual* (Kriegler, 1990).

Numeric ranges provided herein are inclusive of the numbers defining the range.

Unless otherwise indicated, nucleic acids are written left to right in 5' to 3' orientation; amino acid sequences are written left to right in amino to carboxy orientation, respectively.

Definitions

"A," "an" and "the" include plural references unless the context clearly dictates otherwise.

The term "adaptor" herein refers to a nucleic acid that is attached to both strands of a double-stranded DNA molecule. The adaptor can be composed of two distinct oligonucleotide molecules that are base-paired with one another, i.e., complementary. Alternatively, the adaptor can be composed of a single oligonucleotide that includes one or more regions of complementarity, and one or more non-complementary regions.

In general, as used herein, a sequence element located "at the 3' end" includes the 3'-most nucleotide of the oligonucleotide, and a sequence element located "at the 5' end" includes the 5'-most nucleotide of the oligonucleotide.

As used herein, the term "barcode" (also termed single molecule identifier (SMI)) refers to a known nucleic acid sequence that allows some feature of a polynucleotide with which the barcode is associated to be identified. In some embodiments, the feature of the polynucleotide to be identified is the sample from which the polynucleotide is derived. In some embodiments, barcodes are about or at least about 3, 4, 5, 6, 7, 8, 9, 10, 11, 12, 13, 14, 15, or more nucleotides in length. In some embodiments, barcodes are shorter than 10, 9, 8, 7, 6, 5, or 4 nucleotides in length. In some embodiments, barcodes associated with some polynucleotides are of different lengths than barcodes associated with other polynucleotides. In general, barcodes are of sufficient length and include sequences that are sufficiently different to allow the identification of samples based on barcodes with which they are associated. In some embodiments, a barcode, and the sample source with which it is associated, can be identified accurately after the mutation, insertion, or deletion of one or more nucleotides in the barcode sequence, such as the mutation, insertion, or deletion of 1, 2, 3, 4, 5, 6, 7, 8, 9, 10, or more nucleotides. In some embodiments, each barcode in a plurality of barcodes differ from every other barcode in the plurality at at least three nucleotide positions, such as at least 3, 4, 5, 6, 7, 8, 9, 10, or more nucleotide positions. A plurality of barcodes may be represented in a pool of samples, each sample including polynucleotides comprising one or more barcodes that differ from the barcodes contained in the polynucleotides derived from the other samples in the pool. Samples of polynucleotides including one or more barcodes can be pooled based on the barcode sequences to which they are joined, such that all four of the nucleotide bases A, G, C, and T are approximately evenly represented at one or more positions along each barcode in the pool (such as at 1, 2, 3, 4, 5, 6, 7, 8, or more positions, or all positions of the barcode).

A "sample barcode" or "sample index" refers to a nucleic acid sequence, e.g., an index sequence, that identifies a sample or source of a sample uniquely.

A "molecular barcode" or "molecular index" refers to a nucleic acid sequence that identifies an individual nucleic acid molecule, e.g., the specific nucleic acid sequence of a molecule from a specific individual.

A "blocking group" is any modification that prevents extension of a 3' end of an oligonucleotide, such as by a polymerase, a ligase, and/or other enzymes.

The term "base pair" or "bp" as used herein refers to a partnership (i.e., hydrogen bonded pairing) of adenine (A) with thymine (T), or of cytosine (C) with guanine (G) in a double stranded DNA molecule. In some embodiments, a base pair may include A paired with Uracil (U), for example, in a DNA/RNA duplex.

A "causal genetic variant" is a genetic variant for which there is statistical, biological, and/or functional evidence of association with a disease or trait.

In general, a "complement" of a given nucleic acid sequence is a sequence that is fully complementary to and hybridizable to the given sequence. In general, a first sequence that is hybridizable to a second sequence or set of second sequences is specifically or selectively hybridizable to the second sequence or set of second sequences, such that hybridization to the second sequence or set of second sequences is preferred (e.g., thermodynamically more stable under a given set of conditions, such as stringent conditions commonly used in the art) in comparison with hybridization with non-target sequences during a hybridization reaction. Typically, hybridizable sequences share a degree of sequence complementarity over all or a portion of their respective lengths, such as 25%-100% complementarity, including at least about 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, and 100% sequence complementarity.

The term "complementary" herein refers to the broad concept of sequence complementarity in duplex regions of a single polynucleotide strand or between two polynucleotide strands between pairs of nucleotides through base-pairing. It is known that an adenine nucleotide is capable of forming specific hydrogen bonds ("base pairing") with a nucleotide, which is thymine or uracil. Similarly, it is known that a cytosine nucleotide is capable of base pairing with a guanine nucleotide. However, in certain circumstances, hydrogen bonds may also form between other pairs of bases, e.g., between adenine and cytosine, etc. "Essentially complementary" herein refers to sequence complementarity in duplex regions of a single polynucleotide strand or between two polynucleotide strands, for example, wherein the complementarity is less than 100% but is greater than 90%, and retains the stability of the duplex region.

The term "derived from" encompasses the terms "originated from," "obtained from," "obtainable from," "isolated from," and "created from," and generally indicates that one specified material finds its origin in another specified material or has features that can be described with reference to the another specified material.

The term "duplex" herein refers to a region of complementarity that exists between two polynucleotide sequences. The term "duplex region" refers to the region of sequence complementarity that exists between two oligonucleotides or two portions of a single oligonucleotide.

The term "end-repaired DNA" herein refers to DNA that has been subjected to enzymatic reactions in vitro to blunt-end 5'- and/or 3'-overhangs. Blunt ends can be obtained by filling in missing bases for a strand in the 5' to 3' direction using a polymerase, and by removing 3'-overhangs using an exonuclease. For example, T4 polymerase and/or Klenow DNA polymerase may be used for DNA end repair.

The terms "first end" and "second end" when used in reference to a nucleic acid molecule, herein refers to ends of a linear nucleic acid molecule.

A "gene" refers to a DNA segment that is involved in producing a polypeptide and includes regions preceding and following the coding regions as well as intervening sequences (introns) between individual coding segments (exons).

"Hybridization" and "annealing" refer to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. The complex may include two nucleic acid strands forming a duplex structure, three or more strands forming a multi-stranded complex, a single self-hybridizing strand, or any combination of these. A hybridization reaction may constitute a step in a more extensive process, such as the initiation of polymerase chain reaction (PCR), ligation reaction, sequencing reaction, or cleavage reaction, e.g., enzymatic cleavage of a polynucleotide by a ribozyme. A first nucleic acid sequence that can be stabilized via hydrogen bonding with the bases of the nucleotide residues of a second sequence is said to be "hybridizable" to the second sequence. In such a case, the second sequence can also be said to be hybridizable to the first sequence. The term "hybridized" refers to a polynucleotide in a complex that is stabilized via hydrogen bonding between the bases of the nucleotide residues.

When referring to immobilization or attachment of molecules (e.g., nucleic acids) to a solid support, the terms "immobilized" and "attached" are used interchangeably herein, and both terms are intended to encompass direct or indirect, covalent or non-covalent attachment, unless indicated otherwise. In some embodiments, covalent attachment may be preferred, but generally all that is required is that the molecules (e.g., nucleic acids) remain immobilized or attached to the support under the conditions in which it is intended to use the support, for example in nucleic acid amplification and/or sequencing applications.

The terms "isolated," "purified," "separated," and "recovered" as used herein refer to a material (e.g., a protein, nucleic acid, or cell) that is removed from at least one component with which it is naturally associated, for example, at a concentration of at least 90% by weight, or at least 95% by weight, or at least 98% by weight of the sample in which it is contained. For example, these terms may refer to a material which is substantially or essentially free from components which normally accompany it as found in its native state, such as, for example, an intact biological system. An isolated nucleic acid molecule includes a nucleic acid molecule contained in cells that ordinarily express the nucleic acid molecule, but the nucleic acid molecule is present extrachromosomally or at a chromosomal location that is different from its natural chromosomal location.

The terms "joining" and "ligation" as used herein, with respect to two polynucleotides, such as an adapter oligonucleotide and a sample polynucleotide, refers to the covalent attachment of two separate polynucleotides to produce a single larger polynucleotide with a contiguous backbone.

The term "library" herein refers to a collection or plurality of template molecules, i.e., target DNA duplexes, which share common sequences at their 5' ends and common sequences at their 3' ends. Use of the term "library" to refer to a collection or plurality of template molecules should not be taken to imply that the templates making up the library are derived from a particular source, or that the "library" has a particular composition. By way of example, use of the term "library" should not be taken to imply that the individual templates within the library must be of different nucleotide sequence or that the templates must be related in terms of sequence and/or source.

The term "mutation" herein refers to a change introduced into a parental sequence, including, but not limited to, substitutions, insertions, deletions (including truncations). The consequences of a mutation include, but are not limited to, the creation of a new character, property, function, phenotype or trait not found in the protein encoded by the parental sequence.

The term "Next Generation Sequencing (NGS)" herein refers to sequencing methods that allow for massively parallel sequencing of clonally amplified and of single nucleic acid molecules during which a plurality, e.g., millions, of nucleic acid fragments from a single sample or from multiple different samples are sequenced in unison. Non-limiting examples of NGS include sequencing-by-synthesis, sequencing-by-ligation, real-time sequencing, and nanopore sequencing.

The term "nucleotide" herein refers to a monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. When the nucleoside contains a phosphate group bonded to the 3' or 5' position of the pentose it is referred to as a nucleotide. A sequence of polymeric operatively linked nucleotides is typically referred to herein as a "base sequence" or "nucleotide sequence," or nucleic acid or polynucleotide "strand," and is represented herein by a formula whose left to right orientation is in the conventional direction of 5'-terminus to 3'-terminus, referring to the terminal 5' phosphate group and the terminal 3' hydroxyl group at the "5'" and "3'" ends of the polymeric sequence, respectively.

The term "nucleotide analog" herein refers to analogs of nucleoside triphosphates, e.g., (S)-Glycerol nucleoside triphosphates (gNTPs) of the common nucleobases: adenine, cytosine, guanine, uracil, and thymidine (Horhota et al., *Organic Letters*, 8:5345-5347 [2006]). Also encompassed are nucleoside tetraphosphate, nucleoside pentaphosphates and nucleoside hexaphosphates.

The term "operably linked" refers to a juxtaposition or arrangement of specified elements that allows them to perform in concert to bring about an effect. For example, a promoter is operably linked to a coding sequence if it controls the transcription of the coding sequence.

The term "polymerase" herein refers to an enzyme that catalyzes the polymerization of nucleotides (i.e., the polymerase activity). The term polymerase encompasses DNA polymerases, RNA polymerases, and reverse transcriptases. A "DNA polymerase" catalyzes the polymerization of deoxyribonucleotides. An "RNA polymerase" catalyzes the polymerization of ribonucleotides. A "reverse transcriptase" catalyzes the polymerization of deoxyribonucleotides that are complementary to an RNA template.

The terms "polynucleotide," "nucleotide," "nucleotide sequence," "nucleic acid," and "oligonucleotide" are used interchangeably. They refer to a polymeric form of nucleotides of any length, either deoxyribonucleotides or ribonucleotides, or analogs thereof. Polynucleotides may have any three-dimensional structure, and may perform any function, known or unknown. and single- or multi-stranded (e.g., single-stranded, double-stranded, triple-helical, etc.), which contain deoxyribonucleotides, ribonucleotides, and/or analogs or modified forms of deoxyribonucleotides or ribonucleotides, including modified nucleotides or bases or their analogs. Because the genetic code is degenerate, more than one codon may be used to encode a particular amino acid, and the present invention encompasses polynucleotides which encode a particular amino acid sequence. Any type of modified nucleotide or nucleotide analog may be used, so long as the polynucleotide retains the desired functionality under conditions of use, including modifications that increase nuclease resistance (e.g., deoxy, 2'-O-Me, phosphorothioates, etc.). Labels may also be incorporated for purposes of detection or capture, for example, radioactive or nonradioactive labels or anchors, e.g., biotin. The term polynucleotide also includes peptide nucleic acids (PNA). Polynucleotides may be naturally occurring or non-naturally occurring. Polynucleotides may contain RNA, DNA, or both, and/or modified forms and/or analogs thereof. A sequence of nucleotides may be interrupted by non-nucleotide components. One or more phosphodiester linkages may be replaced by alternative linking groups. These alternative linking groups include, but are not limited to, embodiments wherein phosphate is replaced by P(O)S ("thioate"), P(S)S ("dithioate"), (O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need and circular portions. The following are nonlimiting examples of polynucleotides: coding or non-coding regions of a gene or gene fragment, intergenic DNA, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), small nucleolar RNA, ribozymes, cDNA, recombinant polynucleotides, branched polynucleotides, plasmids, vectors, isolated DNA of any sequence, isolated RNA of any sequence, nucleic acid probes, adapters, and primers. A polynucleotide may include modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component, tag, reactive moiety, or binding partner. Polynucleotide sequences, when provided, are listed in the 5' to 3' direction, unless stated otherwise.

As used herein, "polypeptide" refers to a composition comprised of amino acids and recognized as a protein by those of skill in the art. The conventional one-letter or three-letter code for amino acid residues is used herein. The terms "polypeptide" and "protein" are used interchangeably herein to refer to polymers of amino acids of any length. The polymer may be linear or branched, it may include modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art.

The term "primer" herein refers to an oligonucleotide, whether occurring naturally or produced synthetically, which is capable of acting as a point of initiation of nucleic acid synthesis when placed under conditions in which synthesis of a primer extension product which is complementary to a nucleic acid strand is induced, e.g., in the presence of four different nucleotide triphosphates and a polymerase enzyme, e.g., a thermostable enzyme, in an appropriate buffer ("buffer" includes pH, ionic strength, cofactors, etc.) and at a suitable temperature. The primer is preferably single-stranded for maximum efficiency in amplification, but may alternatively be double-stranded. If double-stranded, the primer is first treated to separate its strands before being used to prepare extension products. Preferably, the primer is an oligodeoxyribonucleotide. The primer must be sufficiently long to prime the synthesis of extension products in the presence of the polymerase, e.g., thermostable polymerase enzyme. The exact lengths of a primer will depend on many factors, including temperature, source of primer and use of the method. For example, depending on the complexity of the target sequence, the oligonucleotide primer typically contains 15-25 nucleotides, although it may contain more or few nucleotides. Short primer molecules generally require colder temperatures to form sufficiently stable hybrid complexes with template.

A "promoter" refers to a regulatory sequence that is involved in binding RNA polymerase to initiate transcription of a gene. A promoter may be an inducible promoter or a constitutive promoter. An "inducible promoter" is a promoter that is active under environmental or developmental regulatory conditions.

The term "sequencing library" herein refers to DNA that is processed for sequencing, e.g., using massively parallel methods, e.g., NGS. The DNA may optionally be amplified to obtain a population of multiple copies of processed DNA, which can be sequenced by NGS.

The term "single stranded overhang" or "overhang" is used herein to refer to a strand of a double stranded (ds) nucleic acid molecule that extends beyond the terminus of the complementary strand of the ds nucleic acid molecule. The term "5' overhang" or "5' overhanging sequence" is used herein to refer to a strand of a ds nucleic acid molecule that extends in a 5' direction beyond the 3' terminus of the complementary strand of the ds nucleic acid molecule. The term "3' overhang" or "3' overhanging sequence" is used herein to refer to a strand of a ds nucleic acid molecule that extends in a 3' direction beyond the 5' terminus of the complementary strand of the ds nucleic acid molecule.

A "spacer" may consist of a repeated single nucleotide (e.g., 1, 2, 3, 4, 5, 6, 7, 8, 9, 10, or more of the same nucleotide in a row), or a sequence of 2, 3, 4, 5, 6, 7, 8, 9, 10, or more nucleotides repeated 1, 2, 3, 4, 5, 6, 7, 8, 9, 10, or more times. A spacer may comprise or consist of a specific sequence, such as a sequence that does not hybridize to any target sequence in a sample. A spacer may comprise or consist of a sequence of randomly selected nucleotides.

The phrases "substantially similar" and "substantially identical" in the context of at least two nucleic acids typically means that a polynucleotide includes a sequence that has at least about 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or even 99.5% sequence identity, in comparison with a reference (e.g., wild-type) polynucleotide or polypeptide. Sequence identity may be determined using known programs such as BLAST, ALIGN, and CLUSTAL using standard parameters. (See, e.g., Altshul et al. (1990) J. Mol. Biol. 215:403-410; Henikoff et al. (1989) Proc. Natl. Acad. Sci. 89:10915; Karin et al. (1993) Proc. Natl. Acad. Sci. 90:5873; and Higgins et al. (1988) Gene 73:237). Software for performing BLAST analyses is publicly available through the National Center for Biotechnology Information. Also, databases may be searched using FASTA (Person et al. (1988) Proc. Natl. Acad. Sci. 85:2444-2448.) In some embodiments, substantially identical nucleic acid molecules hybridize to each other under stringent conditions (e.g., within a range of medium to high stringency).

Nucleic acid "synthesis" herein refers to any in vitro method for making a new strand of polynucleotide or elongating an existing polynucleotide (i.e., DNA or RNA) in a template dependent manner. Synthesis, according to the invention, can include amplification, which increases the number of copies of a polynucleotide template sequence with the use of a polymerase. Polynucleotide synthesis (e.g., amplification) results in the incorporation of nucleotides into a polynucleotide (e.g., extension from a primer), thereby forming a new polynucleotide molecule complementary to the polynucleotide template. The formed polynucleotide molecule and its template can be used as templates to synthesize additional polynucleotide molecules. "DNA synthesis," as used herein, includes, but is not limited to, polymerase chain reaction (PCR), and may include the use of labeled nucleotides, e.g., for probes and oligonucleotide primers, or for polynucleotide sequencing.

The term "tag" refers to a detectable moiety that may be one or more atom(s) or molecule(s), or a collection of atoms and molecules. A tag may provide an optical, electrochemical, magnetic, or electrostatic (e.g., inductive, capacitive) signature.

The term "tagged nucleotide" herein refers to a nucleotide that includes a tag (or tag species) that is coupled to any location of the nucleotide including, but not limited to a phosphate (e.g., terminal phosphate), sugar or nitrogenous base moiety of the nucleotide. Tags may be one or more atom(s) or molecule(s), or a collection of atoms and molecules. A tag may provide an optical, electrochemical, magnetic, or electrostatic (e.g., inductive, capacitive) signature.

The term "target DNA duplex" herein refers to a double stranded DNA molecule that is derived from a sample polynucleotide that is DNA, e.g., genomic or cell-free DNA ("cfDNA"), and/or RNA.

As used herein, the term "target polynucleotide" refers to a nucleic acid molecule or polynucleotide in a population of nucleic acid molecules having a target sequence to which one or more oligonucleotides are designed to hybridize. In some embodiments, a target sequence uniquely identifies a sequence derived from a sample, such as a particular genomic, mitochondrial, bacterial, viral, or RNA (e.g., mRNA, miRNA, primary miRNA, or pre-miRNA) sequence. In some embodiments, a target sequence is a common sequence shared by multiple different target polynucleotides, such as a common adapter sequence joined to different target polynucleotides. "Target polynucleotide" may be used to refer to a double-stranded nucleic acid molecule that includes a target sequence on one or both strands, or a single-stranded nucleic acid molecule including a target sequence, and may be derived from any source of or process for isolating or generating nucleic acid molecules. A target polynucleotide may include one or more (e.g., 1, 2, 3, 4, 5, 6, 7, 8, 9, 10, or more) target sequences, which may be the same or different. In general, different target polynucleotides include different sequences, such as one or more different nucleotides or one or more different target sequences.

The term "template DNA molecule" herein refers to a strand of a nucleic acid from which a complementary nucleic acid strand is synthesized by a DNA polymerase, for example, in a primer extension reaction.

The term "template-dependent manner" refers to a process that involves the template dependent extension of a primer molecule (e.g., DNA synthesis by DNA polymerase). The term "template-dependent manner" typically refers to polynucleotide synthesis of RNA or DNA wherein the sequence of the newly synthesized strand of polynucleotide is dictated by the well-known rules of complementary base pairing (see, for example, Watson, J. D. et al., In: *Molecular Biology of the Gene,* 4th Ed., W. A. Benjamin, Inc., Menlo Park, Calif. (1987)).

Target Nucleic Acids

Target nucleic acid duplex molecules are provided, and prepared for sequencing in methods provided herein. The target nucleic acid duplex may be derived from a source in which the target exists as double-stranded DNA, such as genomic DNA, or it may be prepared from a single-stranded nucleic acid source, such as RNA, e.g., cDNA.

In some embodiments, a sample that includes genomic nucleic acids to which the methods described herein may be applied may a biological sample such as a tissue sample, a biological fluid sample, or a cell sample, and processed fractions thereof. The sample may be from a mammal, for example, a human. A biological fluid sample includes, as non-limiting examples, blood, plasma, serum, sweat, tears, sputum, urine, ear flow, lymph, interstitial fluid, saliva, cerebrospinal fluid, ravages, bone marrow suspension, vaginal flow, transcervical lavage, brain fluid, ascites, milk, secretions of the respiratory, intestinal and genitourinary tracts, amniotic fluid and leukophoresis samples. In some embodiments, the source sample is a sample that is easily obtainable by non-invasive procedures, e.g., blood, plasma, serum, sweat, tears, sputum, urine, ear flow, or saliva. In some embodiments, the biological sample is a peripheral blood sample, or the plasma and serum fractions. In other embodiments, the biological sample is a swab or smear, a biopsy specimen, or a cell culture. In another embodiment, the sample is a mixture of two or more biological samples, e.g., a biological sample comprising two or more of a biological fluid sample, a tissue sample, and a cell culture sample. As used herein, the terms "blood," "plasma" and "serum" expressly encompass fractions or processed portions thereof. Similarly, where a sample is taken from a biopsy, swab, smear, etc., the "sample" expressly encompasses a processed fraction or portion derived from the biopsy, swab, smear, etc.

In some embodiments, samples can be obtained from sources, including, but not limited to, samples from different individuals, different developmental stages of the same or different individuals, different diseased individuals (e.g., individuals with cancer or suspected of having a genetic disorder), normal individuals, samples obtained at different stages of a disease in an individual, samples obtained from an individual subjected to different treatments for a disease, samples from individuals subjected to different environmental factors, or individuals with predisposition to a pathology, individuals with exposure to a pathogen such as an infectious disease agent (e.g., HIV), and individuals who are recipients of donor cells, tissues and/or organs. In some embodiments, the sample is a sample that includes a mixture of different source samples derived from the same or different subjects. For example, a sample can include a mixture of cells derived from two or more individuals, as is often found at crime scenes. In one embodiment, the sample is a maternal sample that is obtained from a pregnant female, for example a pregnant human woman. In this instance, the sample can be analyzed using the methods described herein to provide a prenatal diagnosis of potential fetal disorders. Unless otherwise specified, a maternal sample includes a mixture of fetal and maternal DNA, e.g., cfDNA. In some embodiments, the maternal sample is a biological fluid sample, e.g., a blood sample. In other embodiments, the maternal sample is a purified cfDNA sample.

A sample can be an unprocessed biological sample, e.g., a whole blood sample. A source sample can be a partially processed biological sample, e.g., a blood sample that has been fractionated to provide a substantially cell-free plasma fraction. A source sample can be a biological sample containing purified nucleic acids, e.g., a sample of purified cfDNA derived from an essentially cell-free plasma sample. Processing of the samples can include freezing samples, e.g., tissue biopsy samples, fixing samples e.g. formalin-fixing, and embedding samples, e.g., paraffin-embedding. Partial processing of samples include sample fractionation, e.g., obtaining plasma fractions from blood samples, and other processing steps required for analyses of samples collected during routine clinical work, in the context of clinical trials, and/or scientific research. Additional processing steps can include steps for isolating and purifying sample nucleic acids. Further processing of purified samples includes, for example, steps for the requisite modification of sample nucleic acids in preparation for sequencing. Preferably, the sample is an unprocessed or a partially processed sample.

Samples can also be obtained from in vitro cultured tissues, cells, or other polynucleotide-containing sources. The cultured samples can be taken from sources including, but not limited to, cultures (e.g., tissue or cells) maintained in different media and/or conditions (e.g., pH, pressure, or temperature), maintained for different periods of time, and/or treated with different factors or reagents (e.g., a drug candidate, or a modulator), or mixed cultures of different types of tissue or cells.

Biological samples can be obtained from a variety of subjects, including but not limited to, mammals, e.g., humans, and other organisms, including, plants, or cells from the subjects, or microorganisms (e.g., bacteria, fungi).

Sample polynucleotides that can be prepared for sequencing and analyzed as described herein include genomic cellular DNA, cell-free DNA, mitochondrial DNA, RNA, and cDNA. Preparation of sequencing libraries for some NGS sequencing platforms require that the polynucleotides be of a specific range of fragment sizes, and require that large polynucleotides, e.g., cellular genomic DNA be fragmented. Fragmentation of polynucleotide molecules by mechanical means cleaves the DNA backbone at C—O, P—O and C—C results in a heterogeneous mix of blunt and 3'- and 5'-overhanging ends with broken C—O, P—O and/or C—C bonds (Alnemri and Litwack (1990) *J Biol Chem* 265:17323-17333; Richards and Boyer (1965) *J Mol Biol* 11:327-340), which need to be repaired for the subsequent enzymatic reactions, e.g., ligation of sequencing adaptors, that are required for preparing DNA for sequencing. Therefore, fragmentation of polynucleotides, e.g., cellular genomic DNA, may be required. Alternatively, fragmentation of cfDNA, which exists as fragments of <300 bases, may not necessary for generating a sequencing library using cfDNA samples.

Samples from which the target polynucleotides are derived can include multiple samples from the same individual, samples from different individuals, or combinations thereof. In some embodiments, a sample includes a plurality of polynucleotides from a single individual. In some embodiments, a sample includes a plurality of polynucleotides from two or more individuals. An individual is any organism or portion thereof from which target polynucleotides can be derived, non-limiting examples of which include plants, animals, fungi, protists, monerans, viruses, mitochondria, and chloroplasts. Sample polynucleotides can be isolated from a subject, such as a cell sample, tissue sample, fluid sample, or organ sample derived therefrom (or cell cultures derived from any of these), including, for example, cultured cell lines, biopsy, blood sample, cheek swab, or fluid sample containing a cell (e.g., saliva). The subject may be an animal, including but not limited to, a cow, a pig, a mouse, a rat, a chicken, a cat, a dog, etc., and is usually a mammal, such as a human. In some embodiments, samples include DNA. In some embodiments, samples include genomic DNA. In some embodiments, samples include mitochondrial DNA, chloroplast DNA, plasmid DNA, bacterial artificial chromosomes, yeast artificial chromosomes, oligonucleotide tags, or combinations thereof. In some embodiments, the samples include DNA generated by amplification, such as by primer extension reactions using any suitable combination of primers and a DNA polymerase, including but not limited to polymerase chain reaction (PCR), reverse transcription, and combinations thereof. Where the template for the primer extension reaction is RNA, the product of reverse transcription is referred to as complementary DNA (cDNA). Primers useful in primer extension reactions can include sequences specific to one or more targets, random sequences, partially random sequences, and combinations thereof. Reaction conditions suitable for primer extension reactions are known in the art. In general, sample polynucleotides include any polynucleotide present in a sample, which may or may not include target polynucleotides. In some embodiments, a sample from a single individual is divided into multiple separate samples (e.g. 2, 3, 4, 5, 6, 7, 8, 9, 10, or more separate samples) that are subjected to the methods described herein independently, such as analysis in duplicate, triplicate, quadruplicate, or more.

Methods for the extraction and purification of nucleic acids are well known in the art. For example, nucleic acids can be purified by organic extraction with phenol, phenol/chloroform/isoamyl alcohol, or similar formulations, including TRIzol and TriReagent. Other non-limiting examples of extraction techniques include: (1) organic extraction followed by ethanol precipitation, e.g., using a phenol/chloroform organic reagent, with or without the use of an automated nucleic acid extractor; (2) stationary phase adsorption; and (3) salt-induced nucleic acid precipitation methods, such precipitation methods being typically referred to as "salting-out" methods. Another example of nucleic acid isolation and/or purification includes the use of magnetic particles to which nucleic acids can specifically or non-specifically bind, followed by isolation of the beads using a magnet, and washing and eluting the nucleic acids from the beads. In some embodiments, the above isolation methods may be preceded by an enzyme digestion step to help eliminate unwanted protein from the sample, e.g., digestion with proteinase K, or other like proteases. If desired, RNase inhibitors may be added to the lysis buffer. For certain cell or sample types, it may be desirable to add a protein denaturation/digestion step to the protocol. Purification methods may be directed to isolate DNA, RNA, or both. When both DNA and RNA are isolated together during or subsequent to an extraction procedure, further steps may be employed to purify one or both separately from the other. Sub-fractions of extracted nucleic acids can also be generated, for example, purification by size, sequence, or other physical or chemical characteristic. In addition to an initial nucleic acid isolation step, purification of nucleic acids can be performed after any step in the methods of the invention, such as to remove excess or unwanted reagents, reactants, or products. Methods for determining the amount and/or purity of nucleic acids in a sample are known in the art, and include absorbance (e.g., absorbance of light at 260 nm, 280 nm, and a ratio of these) and detection of a label (e.g., fluorescent dyes and intercalating agents, such as SYBR green, SYBR blue, DAPI, propidium iodine, Hoechst stain, SYBR gold, ethidium bromide).

In some embodiments, polynucleotides are fragmented into a population of fragmented polynucleotides of one or more specific size range(s). In some embodiments, the amount of sample polynucleotides subjected to fragmentation is about, less than about, or more than about 50 ng, 100 ng, 200 ng, 300 ng, 400 ng, 500 ng, 600 ng, 700 ng, 800 ng, 900 ng, 1000 ng, 1500 ng, 2000 ng, 2500 ng, 5000 ng, 10 .mu.g, or more. In some embodiments, fragments are generated from about, less than about, or more than about 1, 10, 100, 1000, 10000, 100000, 300000, 500000, or more genome-equivalents of starting DNA. Fragmentation may be accomplished by methods known in the art, including chemical, enzymatic, and mechanical fragmentation. In some embodiments, the fragments have an average or median length from about 10 to about 10,000 nucleotides. In some embodiments, the fragments have an average or median length from about 50 to about 2,000 nucleotides. In some embodiments, the fragments have an average or median length of about, less than about, more than about, or about 100 to about 2500, about 200 to about 1000, about 10 to about 800, about 10 to about 500, about 50 to about 500, about 50 to about 250, or about 50 to about 150 nucleotides (e.g., base pairs). In some embodiments, the fragments have an average or median length of about 300 to about 800 nucleotides (e.g., base pairs). In some embodiments, the fragments have an average or median length of about, less than about, or more than about 200, 300, 500, 600, 800, 1000, 1500 or more nucleotides (e.g., base pairs). In some embodiments, the fragmentation is accomplished mechanically, including subjecting sample polynucleotides to acoustic sonication. In some embodiments, the fragmentation includes treating the sample polynucleotides with one or more enzymes under conditions suitable for the one or more enzymes to generate double-stranded nucleic acid breaks. Examples of enzymes useful in the generation of polynucleotide fragments include sequence specific and non-sequence specific nucleases. Non-limiting examples of nucleases include DNase I, Fragmentase, restriction endonucleases, variants thereof, and combinations thereof. For example, digestion with DNase I can induce random double-stranded breaks in DNA in the absence of $Mg^{2+}$ and in the presence of $Mn^{2+}$. In some embodiments, fragmentation includes treating the sample polynucleotides with one or more restriction endonucleases. Fragmentation can produce fragments having 5' overhangs, 3' overhangs, blunt ends, or a combination thereof. In some embodiments, such as when fragmentation includes the use of one or more restriction endonucleases, cleavage of sample polynucleotides leaves overhangs having a predictable sequence. In some embodiments, the method includes the step of size selecting the fragments via standard methods such as column purification or isolation from an agarose gel. In some embodiments, the method includes determining the average and/or median fragment length after fragmentation. In some embodiments, samples having an average and/or median fragment length above a desired threshold are again subjected to fragmentation. In some embodiments, samples having an average and/or median fragment length below a desired threshold are discarded.

In some embodiments, the 5' and/or 3' end nucleotide sequences of fragmented polynucleotides are not modified prior to ligation with one or more adapter oligonucleotides. For example, fragmentation by a restriction endonuclease can be used to leave a predictable overhang, followed by ligation with one or more adapter oligonucleotides having an overhang complementary to the predictable overhang on a polynucleotide fragment. In another example, cleavage by an enzyme that leaves a predictable blunt end can be followed by ligation of blunt-ended polynucleotide fragments to adapter oligonucleotides that include a blunt end. In some embodiments, the fragmented polynucleotides are blunt-end polished (or "end repaired") to produce polynucleotide fragments having blunt ends, prior to being joined to adapters. Polynucleotide fragments having an overhang can be joined to one or more adapter oligonucleotides having a complementary overhang, such as in a ligation reaction. For example, a single adenine can be added to the 3' ends of end repaired polynucleotide fragments using a template independent polymerase, followed by ligation to one or more adapters each having an overhanging thymine at a 3' end. In some embodiments, adapter oligonucleotides can be joined to blunt end double-stranded DNA fragment molecules which have been modified by extension of the 3' end with one or more nucleotides followed by 5' phosphorylation. In some cases, extension of the 3' end may be performed with a polymerase such as for example Klenow polymerase or any other suitable polymerases known in the art, or by use of a terminal deoxynucleotide transferase, in the presence of one or more dNTPs in a suitable buffer containing magnesium. In some embodiments, target polynucleotides having blunt ends are joined to one or more adapters comprising a blunt end. Phosphorylation of 5' ends of fragmented polynucleotides may be performed for example with T4 polynucleotide kinase in a suitable buffer containing ATP and magnesium. The fragmented polynucleotides may optionally be treated to dephosphorylate 5' ends or 3' ends, for example, by using enzymes known in the art, such as phosphatases.

In some embodiments, the target sequence includes a variant, e.g., a causal genetic variant. A single causal genetic variant can be associated with more than one disease or trait. In some embodiments, a causal genetic variant can be associated with a Mendelian trait, a non-Mendelian trait, or both. Causal genetic variants can manifest as variations in a polynucleotide, such as at least about 1, 2, 3, 4, 5, 6, 7, 8, 9, 10, 20, 50, or more sequence differences (such as between a polynucleotide including the causal genetic variant and a polynucleotide lacking the causal genetic variant at the same relative genomic position). Non-limiting examples of types of causal genetic variants include single nucleotide polymorphisms (SNP), deletion/insertion polymorphisms (DIP), copy number variants (CNV), short tandem repeats (STR), restriction fragment length polymorphisms (RFLP), simple sequence repeats (SSR), variable number of tandem repeats (VNTR), randomly amplified polymorphic DNA (RAPD), amplified fragment length polymorphisms (AFLP), inter-retrotransposon amplified polymorphisms (IRAP), long and short interspersed elements (LINE/SINE), long tandem repeats (LTR), mobile elements, retrotransposon microsatellite amplified polymorphisms, retrotransposon-based insertion polymorphisms, sequence specific amplified polymorphism, and heritable epigenetic modification (for example, DNA methylation). A causal genetic variant may also be a set of closely related causal genetic variants. Some causal genetic variants may exert influence as sequence variations in RNA polynucleotides. At this level, some causal genetic variants are also indicated by the presence or absence of a species of RNA polynucleotides. Also, some causal genetic variants result in sequence variations in protein polypeptides. A number of causal genetic variants are known in the art. An example of a causal genetic variant that is a SNP is the Hb S variant of hemoglobin that causes sickle cell anemia. An example of a causal genetic variant that is a DIP is the delta508 mutation of the CFTR gene which causes cystic fibrosis. An example of a causal genetic variant that is a CNV is trisomy 21, which causes Down's syndrome. An example of a causal genetic variant that is an STR is tandem repeat that causes Huntington's disease. Non-limiting examples of causal genetic variants are described in US2010/0022406, which is incorporated by reference in its entirety.

Causal genetic variants can be originally discovered by statistical and molecular genetic analyses of the genotypes and phenotypes of individuals, families, and populations. The causal genetic variants for Mendelian traits are typically identified in a two-stage process. In the first stage, families are identified in which multiple individuals who possess the trait are examined for genotype and phenotype. Genotype and phenotype data from these families is used to establish the statistical association between the presence of the Mendelian trait and the presence of a number of genetic markers. This association establishes a candidate region in which the causal genetic variant is likely to map. In a second stage, the causal genetic variant itself is identified. The second step typically entails sequencing the candidate region. More sophisticated, one-stage processes are possible with more advanced technologies which permit the direct identification of a causal genetic variant or the identification of smaller candidate regions. After one causal genetic variant for a trait is discovered, additional variants for the same trait can be discovered. For example, the gene associated with the trait can be sequenced in individuals who possess the trait or their relatives. Many causal genetic variants are cataloged in databases including the Online Mendelian Inheritance in Man (OMIM) and the Human Gene Mutation Database (HGMD).

A causal genetic variant may exist at any frequency within a specified population. In some embodiments, a causal genetic variant causes a trait having an incidence of no more than 1% a reference population. In another embodiment, a causal genetic variants causes a trait having an incidence of no more than $1/10,000$ in a reference population.

In some embodiments, a causal genetic variant which is associated with a disease or trait is a genetic variant, the presence of which increases the risk of having or developing the disease or trait by about, less than about, or more than about 1%, 5%, 10%, 15%, 20%, 25%, 30%, 40%, 50%, 60%, 70%, 80%, 90%, 100%, 200%, 300%, 400%, 500%, or more. In some embodiments, a causal genetic variant is a genetic variant the presence of which increases the risk of having or developing a disease or trait by about, less than about, or more than about 1-fold, 2-fold, 3-fold, 4-fold, 5-fold, 6-fold, 7-fold, 8-fold, 9-fold, 10-fold, 25-fold, 50-fold, 100-fold, 500-fold, 1000-fold, 10000-fold, or more. In some embodiments, a causal genetic variant is a genetic variant the presence of which increases the risk of having or developing a disease or trait by any statistically significant amount, such as an increase having a p-value of about or less than about 0.1, $0.05^{-3}$, $10^{-4}$, $10^{-5}$, $10^{-6}$, $10^{-7}$, $10^{-8}$, $10^{-9}$, $10^{-10}$, $10^{-11}$, $10^{-12}$, $10^{-13}$, $10^{-14}$, $10^{-15}$, or smaller.

In some embodiments, a causal genetic variant has a different degree of association with a disease or trait between two or more different populations of individuals, such as between two or more human populations. In some embodiments, a causal genetic variant has a statistically significant association with a disease or trait only within one or more populations, such as one or more human populations. A human population can be a group of people sharing a common genetic inheritance, such as an ethnic group. A human population can be a haplotype population or group of haplotype populations. A human population can be a national group. A human population can be a demographic population such as those delineated by age, gender, and socioeconomic factors. Human populations can be historical populations. A population can consist of individuals distributed over a large geographic area such that individuals at extremes of the distribution may never meet one another. The individuals of a population can be geographically dispersed into discontinuous areas. Populations can be informative about biogeographical ancestry. Populations can also be defined by ancestry. Genetic studies can define populations. In some embodiments, a population may be based on ancestry and genetics. A sub-population may serve as a population for the purpose of identifying a causal genetic variant.

In some embodiments, a causal genetic variant is associated with a disease, such as a rare genetic disease. Examples of rare genetic diseases include, but are not limited to: 21-Hydroxylase Deficiency, ABCC8-Related Hyperinsulinism, ARSACS, Achondroplasia, Achromatopsia, Adenosine Monophosphate Deaminase 1, Agenesis of Corpus Callosum with Neuronopathy, Alkaptonuria, Alpha-1-Antitrypsin Deficiency, Alpha-Mannosidosis, Alpha-Sarcoglycanopathy, Alpha-Thalassemia, Alzheimers, Angiotensin II Receptor, Type I, Apolipoprotein E Genotyping, Argininosuccinicaciduria, Aspartylglycosaminuria, Ataxia with Vitamin E Deficiency, Ataxia-Telangiectasia, Autoimmune Polyendocrinopathy Syndrome Type 1, BRCA1 Hereditary Breast/Ovarian Cancer, BRCA2 Hereditary Breast/Ovarian Cancer, Bardet-Biedl Syndrome, Best Vitelliform Macular Dystrophy, Beta-Sarcoglycanopathy, Beta-Thalassemia, Biotinidase Deficiency, Blau Syndrome, Bloom Syndrome, CFTR-Related Disorders, CLN3-Related Neuronal Ceroid-Lipofuscinosis, CLNS-Related Neuronal Ceroid-Lipofuscinosis, CLN8-Related Neuronal Ceroid-Lipofuscinosis, Canavan Disease, Carnitine Palmitoyltransferase IA Deficiency, Carnitine Palmitoyltransferase II Deficiency, Cartilage-Hair Hypoplasia, Cerebral Cavernous Malformation, Choroideremia, Cohen Syndrome, Congenital Cataracts, Facial Dysmorphism, and Neuropathy, Congenital Disorder of Glycosylationla, Congenital Disorder of Glycosylation Ib, Congenital Finnish Nephrosis, Crohn Disease, Cystinosis, DFNA 9 (COCH), Diabetes and Hearing Loss, Early-Onset Primary Dystonia (DYTI), Epidermolysis Bullosa Junctional, Herlitz-Pearson Type, FANCC-Related Fanconi Anemia, FGFR1-Related Craniosynostosis, FGFR2-Related Craniosynostosis, FGFR3-Related Craniosynostosis, Factor V Leiden Thrombophilia, Factor V R2 Mutation Thrombophilia, Factor XI Deficiency, Factor XIII Deficiency, Familial Adenomatous Polyposis, Familial Dysautonomia, Familial Hypercholesterolemia Type B, Familial Mediterranean Fever, Free Sialic Acid Storage Disorders, Frontotemporal Dementia with Parkinsonism-17, Fumarase deficiency, GJB2-Related DFNA 3 Nonsyndromic Hearing Loss and Deafness, GJB2-Related DFNB 1 Nonsyndromic Hearing Loss and Deafness, GNE-Related Myopathies, Galactosemia, Gaucher Disease, Glucose-6-Phosphate Dehydrogenase Deficiency, Glutaricacidemia Type 1, Glycogen Storage Disease Type 1a, Glycogen Storage Disease Type Ib, Glycogen Storage Disease Type II, Glycogen Storage Disease Type III, Glycogen Storage Disease Type V, Gracile Syndrome, HFE-Associated Hereditary Hemochromatosis, Halder AIMs, Hemoglobin S Beta-Thalassemia, Hereditary Fructose Intolerance, Hereditary Pancreatitis, Hereditary Thymine-Uraciluria, Hexosaminidase A Deficiency, Hidrotic Ectodermal Dysplasia 2, Homocystinuria Caused by Cystathionine Beta-Synthase Deficiency, Hyperkalemic Periodic Paralysis Type 1, Hyperornithinemia-Hyperammonemia-Homocitrullinuria Syndrome, Hyperoxaluria, Primary, Type 1, Hyperoxaluria, Primary, Type 2, Hypochondroplasia, Hypokalemic Periodic Paralysis Type 1, Hypokalemic Periodic Paralysis Type 2, Hypophosphatasia, Infantile Myopathy and Lactic Acidosis (Fatal and Non-Fatal Forms), Isovaleric Acidemias, Krabbe Disease, LGMD2I, Leber Hereditary Optic Neuropathy, Leigh Syndrome, French-Canadian Type, Long Chain 3-Hydroxyacyl-CoA Dehydrogenase Deficiency, MELAS, MERRF, MTHFR Deficiency, MTHFR Thermolabile Variant, MTRNR1-Related Hearing Loss and Deafness, MTTS1-Related Hearing Loss and Deafness, MYH-Associated Polyposis, Maple Syrup Urine Disease Type 1A, Maple Syrup Urine Disease Type 1B, McCune-Albright Syndrome, Medium Chain Acyl-Coenzyme A Dehydrogenase Deficiency, Megalencephalic Leukoencephalopathy with Subcortical Cysts, Metachromatic Leukodystrophy, Mitochondrial Cardiomyopathy, Mitochondrial DNA-Associated Leigh Syndrome and NARP, Mucolipidosis IV, Mucopolysaccharidosis Type I, Mucopolysaccharidosis Type IIIA, Mucopolysaccharidosis Type VII, Multiple Endocrine Neoplasia Type 2, Muscle-Eye-Brain Disease, Nemaline Myopathy, Neurological phenotype, Niemann-Pick Disease Due to Sphingomyelinase Deficiency, Niemann-Pick Disease Type C1, Nijmegen Breakage Syndrome, PPT1-Related Neuronal Ceroid-Lipofuscinosis, PROP1-related pituitary hormone deficiency, Pallister-Hall Syndrome, Paramyotonia Congenita, Pendred Syndrome, Peroxisomal Bifunctional Enzyme Deficiency, Pervasive Developmental Disorders, Phenylalanine Hydroxylase Deficiency, Plasminogen Activator Inhibitor I, Polycystic Kidney Disease, Autosomal Recessive, Prothrombin G20210A Thrombophilia, Pseudovitamin D Deficiency Rickets, Pycnodysostosis, Retinitis Pigmentosa, Autosomal Recessive, Bothnia Type, Rett Syndrome, Rhizomelic Chondrodysplasia Punctata Type 1, Short Chain Acyl-CoA Dehydrogenase Deficiency, Shwachman-Diamond Syndrome, Sjogren-Larsson Syndrome, Smith-Lemli-Opitz Syndrome, Spastic Paraplegia 13, Sulfate Transporter-Related Osteochondrodysplasia, TFR2-Related Hereditary Hemochromatosis, TPP1-Related Neuronal Ceroid-Lipofuscinosis, Thanatophoric Dysplasia, Transthyretin Amyloidosis, Trifunctional Protein Deficiency, Tyrosine Hydroxylase-Deficient DRD, Tyrosinemia Type I, Wilson Disease, X-Linked Juvenile Retinoschisis and Zellweger Syndrome Spectrum.

In some embodiments, the target sequence includes a non-subject sequence. In general, a non-subject sequence corresponds to a polynucleotide derived from an organism other than the individual being tested, such as DNA or RNA from bacteria, archaea, viruses, protists, fungi, or other organism. A non-subject sequence may be indicative of the identity of an organism or class of organisms, and may further be indicative of a disease state, such as infection. An example of non-subject sequences useful in identifying an organism include, without limitation, ribosomal RNA (rRNA) sequences, such as 16s rRNA sequences (see, e.g., WO2010/151842). In some embodiments, non-subject sequences are analyzed instead of, or separately from causal genetic variants. In some embodiments, causal genetic variants and non-subject sequences are analyzed in parallel, such as in the same sample and/or in the same report.

Adaptors

Polynucleotide adaptors are provided for use in the methods disclosed herein. Adaptors herein include: (i) a double-stranded region that includes a molecular barcode; and (ii) first and second single-stranded regions. The first single-stranded region and optionally, a portion of the double-stranded region, includes a sequence "S1," that is 5' of the molecular barcode sequence and the second single-stranded region and optionally, a portion of the double-stranded region, includes a sequence "S2'" that is 3' of the molecular barcode sequence. S1 and S2' are different. In some embodiments, the first single-stranded region consists of sequence S1 and the double-stranded region does not comprise a portion of S1. In some embodiments, the second single-stranded region consists of sequence S2' and the double-stranded region does not comprise a portion of S2'. In other embodiments, the double-stranded region comprises a portion of S1 and a complementary portion of S2'.

Figure 1B:
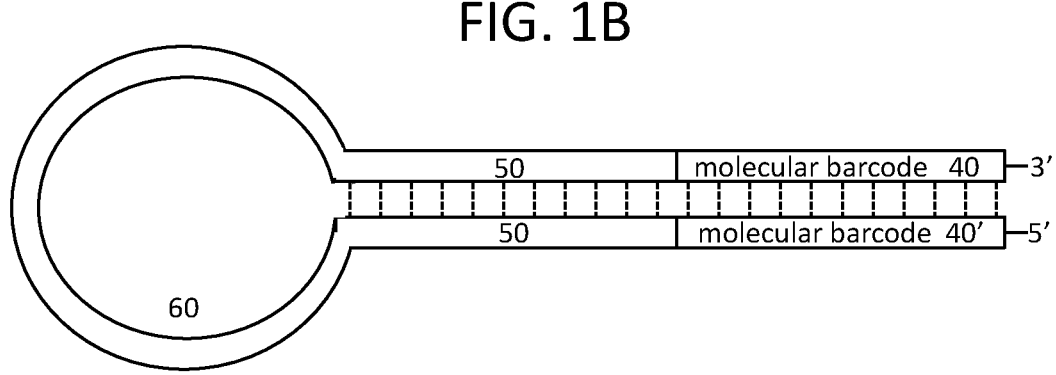
FIG. 1B illustrates one example of a U-shaped sequencing adapter comprising a duplex molecular barcode.

In some embodiments, adaptors are Y-shaped, as shown in FIG. 1A, with first and second single-stranded regions on separate polynucleotides. In other embodiments, adaptors are U-shaped, as shown in FIG. 1B, with a single-stranded hairpin region, and first and second single-stranded regions are on the same polynucleotide. In other embodiments, adaptors include more than one double-stranded region, with single-stranded regions between, with a terminal double-stranded region that includes the molecular barcode.

Figure 8:
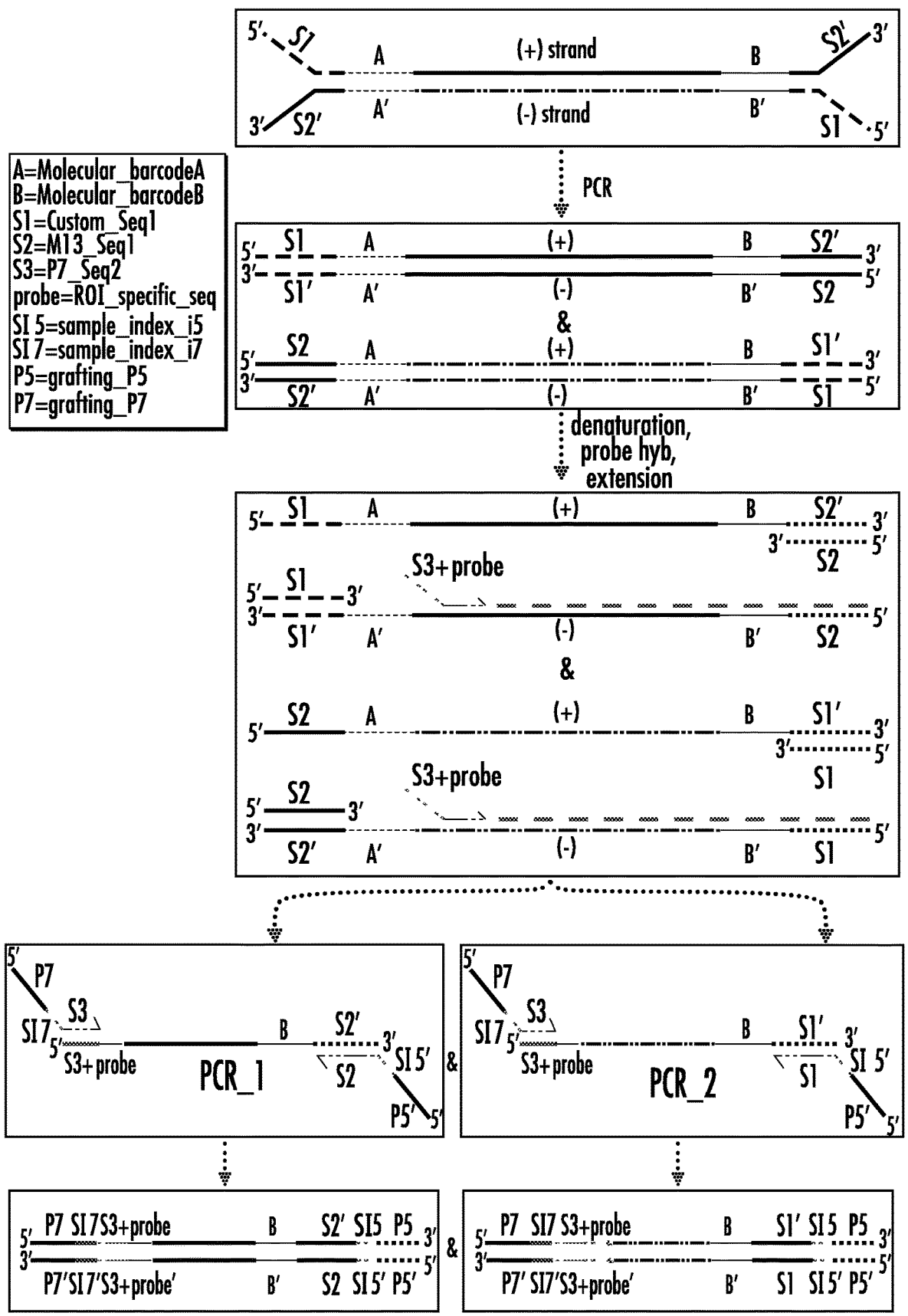
FIG. 8 schematically depicts an embodiment of a nucleic acid sequencing method as described herein.

A plurality of adaptors for use in the methods described herein may all contain the same molecular barcode sequence, or may include different barcode sequences as shown in FIG. 8 (barcode duplex sequences "A" and "A'" and "B" and "B'"). Nonlimiting embodiments of barcode sequences comprise or consist of the polynucleotide sequences depicted in SEQ ID NOs: 1 and 2.

Nonlimiting embodiments of sequences S1 and S2' comprise or consist of the polynucleotide sequences depicted in SEQ ID NOs: 3 and 4.

In some embodiments, a sample index (sample barcode), i.e., specific for a sample, is included in the adaptor upstream or downstream of the molecular barcode. The sample index may be "inline" (introduced via an adaptor rather than via an external probe or primer sequence). For example, an inline sample index may be immediately adjacent to the molecular barcode in an adaptor as described herein. For example, the sample index may be in the double-stranded region of the adaptor, i.e., upstream (between S1 or S2' and the molecular barcode) or downstream (at the terminus of the double stranded region) relative to the molecular barcode sequence in the double-stranded region of the adaptor. In various embodiments of the methods herein, one or more inline sample index(es) may be introduced via one or more adaptor, and/or one or more non-inline sample index(es) may be introduced in a probe or primer sequence such as during amplification of primer extension products as described herein, or a combination of inline sample index(es) and non-inline sample index(es) may be introduced.

Adapter oligonucleotides can include DNA, RNA, nucleotide analogues, non-canonical nucleotides, labeled nucleotides, modified nucleotides, or combinations thereof.

Adaptors may be ligated to first and second ends of a target nucleic acid duplex molecule in simultaneous or sequential reactions.

In some embodiments of the methods herein, fragmentation of polynucleotides is followed by ligation of adapter oligonucleotides to the fragmented polynucleotides. In some embodiments, an adapter is a mismatched adapter formed by annealing two partially complementary polynucleotide strands so as to provide, when the two strands are annealed, at least one double-stranded region that includes the molecular barcode sequence and at least one unmatched region. A "double-stranded region" of the adapter is a short double-stranded region, typically comprising 5 or more consecutive base pairs, formed by annealing of the two partially complementary polynucleotide strands. This term simply refers to a double-stranded region of nucleic acid in which the two strands are annealed and does not imply any particular structural conformation. In some embodiments, a double-stranded region is about, less than about, or more than about 5, 10, 15, 20, 25, 30, or more nucleotides in length. In some embodiments, it is advantageous for the double-stranded region of a mismatched adapter to be as short as possible without loss of function. By "function" in this context is meant that the double-stranded region form a stable duplex under standard reaction conditions for an enzyme-catalyzed nucleic acid ligation reaction, which conditions are known to those skilled in the art (e.g., incubation at a temperature in the range of about 4° C. to about 25° C. in a ligation buffer appropriate for the enzyme), such that the two strands forming the adapter remain partially annealed during ligation of the adapter to a target molecule. It is not absolutely necessary for the double-stranded region to be stable under the conditions typically used in the annealing steps of primer extension or PCR reactions. The terminal double-stranded region is at the "ligatable" end of the adapter, i.e., the end that is joined to a target polynucleotide in a ligation reaction. The ligatable end of the adapter may be blunt or, in other embodiments, short 5' or 3' overhangs of one or more nucleotides may be present to facilitate/promote ligation. The 5' terminal nucleotide at the ligatable end of the adapter is typically phosphorylated to enable phosphodiester linkage to a 3' hydroxyl group on a sample polynucleotide. The term "unmatched region" refers to a region of the adapter wherein the sequences of two polynucleotide strands forming the adapter or a region of a single polynucleotide strand that forms the adaptor exhibit(s) a degree of non-complementarity such that polynucleotide sequences on the two strands or on the single strand are not capable of annealing to each other under standard annealing conditions for a primer extension or PCR reaction. The nucleotide sequences in the unmatched region may exhibit some degree of annealing under standard reaction conditions for an enzyme-catalyzed ligation reaction, provided that they revert to single stranded form under annealing conditions.

In some embodiments, the adapter oligonucleotides joined to target polynucleotides from one sample sequences include common to all adapter oligonucleotides and a barcode that is unique to the adapters joined to polynucleotides of that particular sample, such that the barcode sequence can be used to distinguish polynucleotides originating from one sample or adapter joining reaction from polynucleotides originating from another sample or adapter joining reaction.

In some embodiments, an adapter includes a 5' overhang, a 3' overhang, or both that is complementary to one or more target polynucleotide overhangs. Complementary overhangs can be one or more nucleotides in length, including but not limited to 1, 2, 3, 4, 5, 6, 7, 8, 9, 10, 11, 12, 13, 14, 15, or more nucleotides in length. In some embodiments, an adapter overhang is complementary to a target polynucleotide overhang produced by restriction endonuclease digestion. In some embodiments, an adapter overhang consists of an adenine or a thymine.

Figure 2:
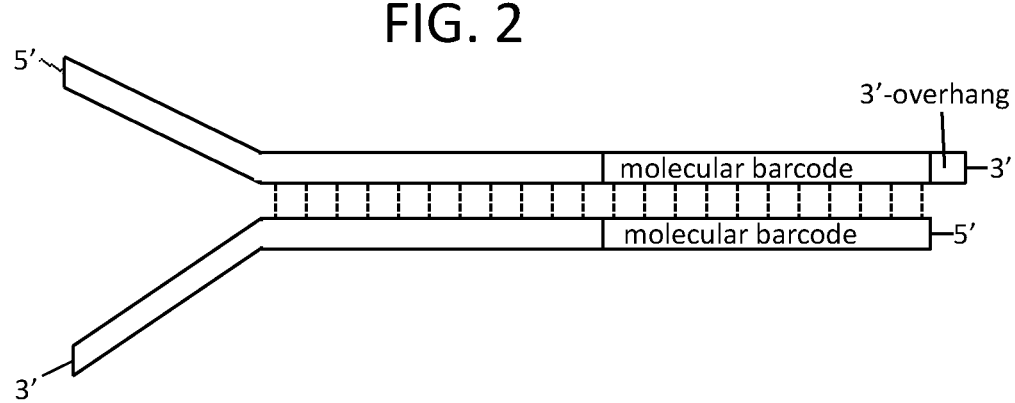
FIG. 2 illustrates one example of a sequencing adapter comprising a duplex molecular barcode and a constant 3'-overhang.
Figure 6:
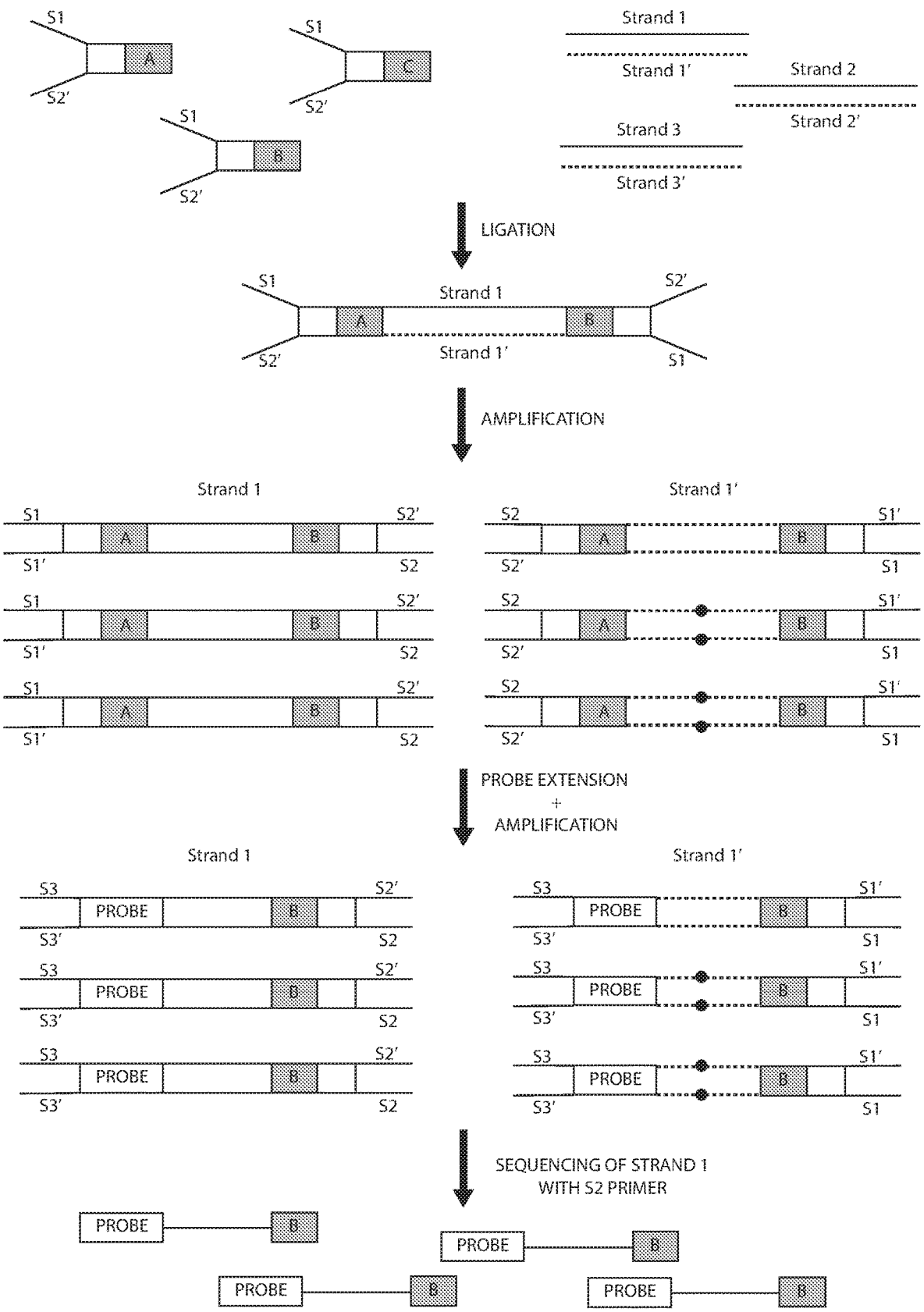
FIG. 6 illustrates one embodiment of a method of sequencing a duplex nucleic acid molecule.

In some embodiments, the sequencing adapter includes a constant 3'-overhang, which can be adjacent to the molecular barcode in the sequencing adapter, as shown schematically in FIG. 6. The constant 3'-overhang is referred to as "constant" because the same 3'-overhang is used for each of the sequencing adapters in a composition. In some embodiments, the constant 3'-overhang can include adenine (A), thymine (T), guanine (G), cytosine (C), uracil (U), inosine (I), or any other natural or synthetic base. In some embodiments, the 3'-overhang includes a dinucleotide, such as a guanine-cytosine (GC) dinucleotide. The constant 3'-overhang can be ligated to the target nucleic acid molecule to be sequenced. FIG. 2 illustrates one exemplary embodiment of a sequencing adapter comprising a constant 3'-overhang. The molecular barcode is ligated adjacent to the nucleic acid molecule to be sequenced, except that it may be separated by the constant 3'-overhang (and/or its complementary base(s) that may be included in the complementary strand after ligation).

In some embodiments, the amount of target nucleic acid duplex molecules, e.g., fragmented polynucleotides subjected to adapter joining is about, less than about, or more than about 50 ng, 100 ng, 200 ng, 300 ng, 400 ng, 500 ng, 600 ng, 700 ng, 800 ng, 900 ng, 1000 ng, 1500 ng, 2000 ng, 2500 ng, 5000 ng, 10 µg, or more (e.g., a threshold amount). In some embodiments, the amount of fragmented polynucleotides is determined before proceeding with adapter joining, where adapter joining is not performed if the amount is below a threshold amount.

Methods for joining two polynucleotides are known in the art, and include without limitation, enzymatic and non-enzymatic (e.g., chemical) methods. Examples of ligation reactions that are non-enzymatic include the non-enzymatic ligation techniques described in U.S. Pat. Nos. 5,780,613 and 5,476,930, which are herein incorporated by reference. In some embodiments, an adapter oligonucleotide is joined to target nucleic acid duplex, e.g., a fragmented polynucleotide, by a ligase, for example a DNA ligase or RNA ligase. Multiple ligases, each having characterized reaction conditions, are known in the art, and include, without limitation $NAD^+$-dependent ligases including tRNA ligase, Taq DNA ligase, *Thermus filiformis* DNA ligase, *Escherichia coli* DNA ligase, Tth DNA ligase, *Thermus scotoductus* DNA ligase (I and II), thermostable ligase, Ampligase thermostable DNA ligase, VanC-type ligase, 9° N DNA Ligase, Tsp DNA ligase, and novel ligases discovered by bioprospecting; ATP-dependent ligases including T4 RNA ligase, T4 DNA ligase, T3 DNA ligase, T7 DNA ligase, Pfu DNA ligase, DNA ligase 1, DNA ligase III, DNA ligase IV, and novel ligases discovered by bioprospecting; and wild-type, mutant isoforms, and genetically engineered variants thereof. Ligation can be between polynucleotides having hybridizable sequences, such as complementary overhangs. Ligation can also be between two blunt ends. Generally, a 5' phosphate is utilized in a ligation reaction. The 5' phosphate can be provided by the fragmented polynucleotide, the adapter oligonucleotide, or both. 5' phosphates can be added to or removed from polynucleotides to be joined, as needed. Methods for the addition or removal of 5' phosphates are known in the art, and include without limitation enzymatic and chemical processes. Enzymes useful in the addition and/or removal of 5' phosphates include kinases, phosphatases, and polymerases. In some embodiments, both of the two ends joined in a ligation reaction (i.e., an adapter end and a target nucleic acid duplex, e.g., fragmented polynucleotide, end) provide a 5' phosphate, such that two covalent linkages are made in joining the two ends. In some embodiments, 3' phosphates are removed prior to ligation.

Molecular Barcodes

The sequencing adapters described herein include a molecular barcode having a nucleic acid duplex with a predetermined or nondegenerate sequence. In some embodiments, a plurality of sequencing adapters described herein include molecular barcodes of two or more different lengths (i.e., variable length barcodes). In some embodiments, the sequencing adapter includes a sample index. In some embodiments, a sample index (sample barcode), i.e., specific for a sample, is included in the adaptor upstream or downstream relative the molecular barcode. The sample index may be inline, for example, adjacent, to the molecular barcode. The sample index sequence may be immediately adjacent to the molecular barcode sequence or may be adjacent with a spacer of about 1 to about 20 nucleotide bases, or any of 1 to about 5, about 5 to about 10, about 10 to about 15, about 15 to about 20, about 1 to about 10, about 5 to about 15, or about 10 to about 20 nucleotide bases, or any of 1, 2, 3, 4, 5, 6, 7, 8, 9, 10, 11, 12, 13, 14, 15, 16, 17, 18, 19, or 20 nucleotide bases separating the two sequences.

Sequencing adapter compositions include a plurality of sequencing adapters, as described herein. The molecular barcodes in a plurality of sequencing adapters are diverse, although multiple copies of the same molecular barcode may be present in a composition including the plurality of sequencing adapters. For example, in some embodiments, the number of unique molecular barcodes in the plurality of sequencing adapters is between 2 and about 500, such as between about 10 and about 400, between about 20 and about 300, between about 50 and about 200, between about 10 and about 50, between about 50 and about 100, between about 75 and about 150, between about 100 and about 200, between about 200 and about 300, between about 300 and about 400, between about 400 and about 500, or about 24, about 48, about 96, about 192, or about 384.

In some embodiments, a molecular barcode in the plurality of sequencing adapters has an edit distance of 2 or more, 3 or more, 4 or more, 5 or more, 6 or more, 7 or more, or 8 or more from any other unique molecular barcode. Edit distance refers to the minimum number of single-base substitutions, single-base insertions, and/or single-base deletions that a pair of sequences must undergo to result in complete identity between the two sequences. For example, if the edit distance between a first molecular barcode and a second molecular barcode is 2, either the first molecular barcode must be mutated at least twice, the second molecular barcode must be mutated at least twice, or the first molecular barcode and the second molecular barcode must be mutated at least once each to result in identical sequences.

The molecular barcodes can be of any length, for example between about 2 and about 24 bases length. In some embodiments, the molecular barcodes are about 2, 3, 4, 5, 6, 7, 8, 9, 10, 11, 12, 13, 14, 15, 16, 17, 18, 19, 20, 21, 22, 23, or 24 bases in length. In some embodiments, the molecular barcodes are about 4 to about 15, or about 12 to about 15 based in length. In some embodiments, a composition includes a plurality of sequencing adapters, and the sequencing adapters include molecular barcodes of at least two different lengths, at least three different lengths, or at least four different lengths. For example, in some embodiments, a plurality of sequencing adapters includes a first sequencing adapter including a first molecular barcode including a nucleic acid duplex n nucleotides in length; and a second sequencing adapter including a second molecular barcode including a nucleic acid duplex n+x nucleotides, wherein x is not zero. In some embodiments, the plurality of sequencing adapters further includes a third sequencing adapter including a third molecular barcode including a nucleic acid duplex n+y nucleotides in length, wherein y is not zero or x.

Variable lengths of the molecular barcodes in the plurality of sequencing adapters are particularly useful, for example, when the sequencing adapters include a constant 3'-overhang. For example, if all molecular barcodes were of the same length, the constant 3'-overhang would be read in the same sequencing cycle, resulting in a large, non-diverse signal. Such non-diverse (or low diverse) signals can be problematic for many sequencing systems, as it can create a high level of noise that overwhelms the true signal at that position. Thus, by using variable length molecular barcodes, it ensures that no single sequencing cycle is presented with only a single base, thereby preventing loss of sequencing quality.

In some embodiments, the molecular barcodes are laser-color balanced. Similar to the variable lengths of the molecular barcodes, laser-color balancing can help ensure that no single sequencing cycle is presented with only a single base when sequencing the molecular barcode. For example, some sequencing systems employ colored lasers to sequence nucleic acid molecules (for example, in some sequencing systems, a green laser is used to sequence G or T nucleotides, and a red laser is used to sequence A or C nucleotides). To avoid oversaturation of signal, resulting in sequencing quality loss, the molecular barcodes can be color balanced. In some embodiments, the molecular barcodes are laser-color balanced amongst the plurality of sequence adapters. For example, in some embodiments, the ratio of A/C to G/T nucleotides at any given position of the molecular barcode in the plurality of sequence adapters is between about 2:1 and about 1:2 (such as about 1:1) at the corresponding position relative to the shortest molecular barcode in the plurality of sequencing adapters. In some embodiments, the molecular barcodes are laser-color balanced within any given molecular barcode. For example, in some embodiments, the ratio of A/C to G/T nucleotides within any given molecular barcode is between about 2:1 and about 1:2 (such as about 1:1).

In some embodiments, the molecular barcodes are base-composition balanced. In some embodiments, the molecular barcodes are base-composition balanced amongst the plurality of sequence adapters. For example, in some embodiments, the proportion of adenine at any given position of the molecular barcode amongst the plurality of sequence adapters is between about 0.2 and about 0.4 (such as between about 0.2 and about 0.3, or about 0.25) at the corresponding position relative to the shortest molecular barcode in the plurality of sequencing adapters; the proportion of cytosine at any given position of the molecular barcodes is between about 0.2 and about 0.4 (such as between about 0.2 and about 0.3, or about 0.25) at the corresponding position relative to the shortest molecular barcode in the plurality of sequencing adapters; the proportion of thymine at any given position of the molecular barcodes is between about 0.2 and about 0.4 (such as between about 0.2 and about 0.3, or about 0.25) at the corresponding position relative to the shortest molecular barcode in the plurality of sequencing adapters; and the proportion of guanine at any given position of the molecular barcodes is between about 0.2 and about 0.4 (such as between about 0.2 and about 0.3, or about 0.25) at the corresponding position relative to the shortest molecular barcode in the plurality of sequencing adapters. In some embodiments, the molecular barcodes are base-composition balanced within the molecular barcode. For example, in some embodiments, the proportion of adenine within any given molecular barcodes is between about 0.2 and about 0.4 (such as between about 0.2 and about 0.3, or about 0.25); the proportion of cytosine within any given molecular barcodes is between about 0.2 and about 0.4 (such as between about 0.2 and about 0.3, or about 0.25); the proportion of thymidine within any given molecular barcodes is between about 0.2 and about 0.4 (such as between about 0.2 and about 0.3, or about 0.25); and the proportion of guanine within any given molecular barcodes is between about 0.2 and about 0.4 (such as between about 0.2 and about 0.3, or about 0.25).

Figure 3:
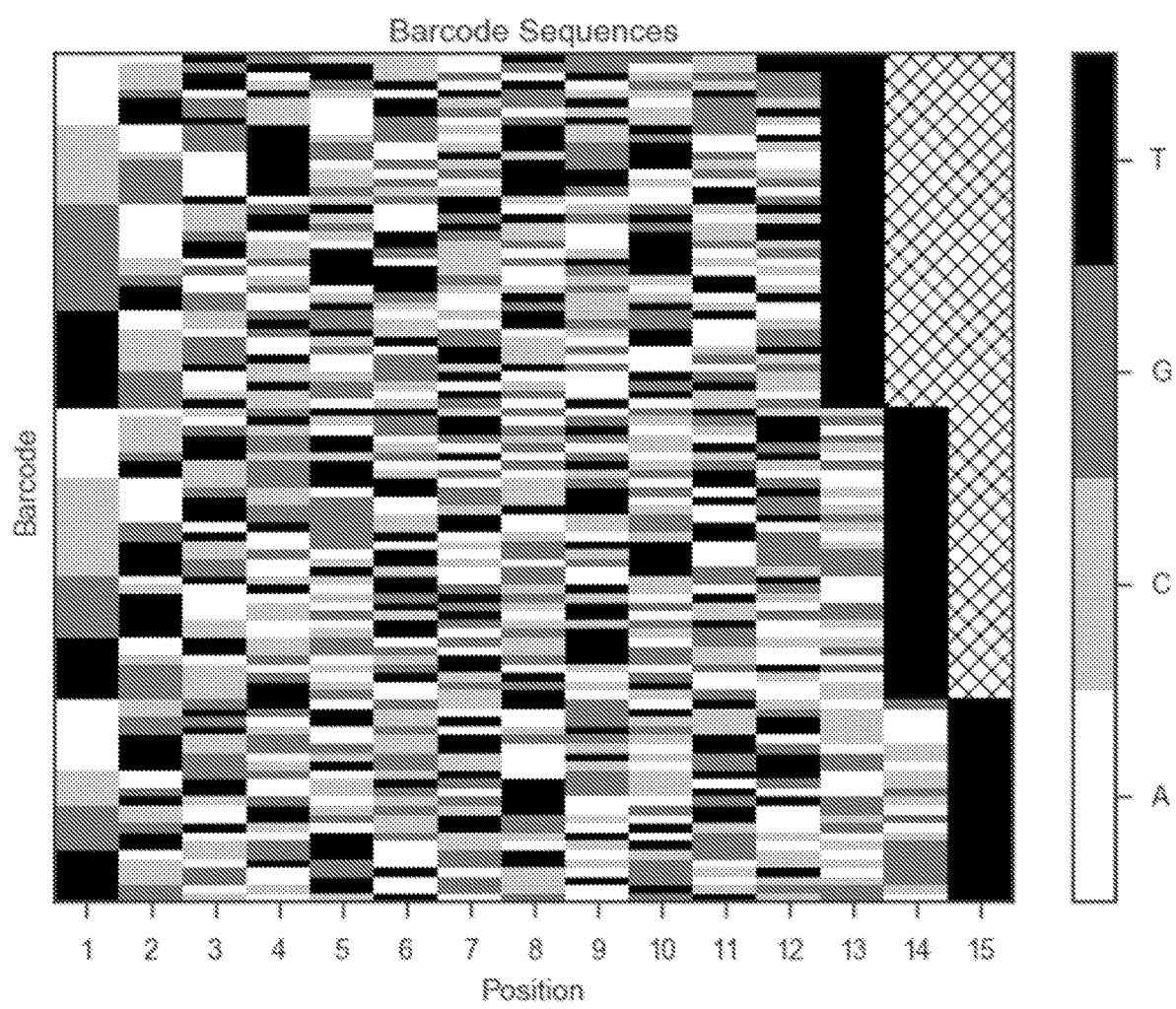
FIG. 3 presents a heatmap showing 96 base-composition balanced molecular barcodes of 12, 13, or 14 nucleotides in length, which precedes a constant 3'-overhang thymine nucleotide. All 96 molecular barcodes are base-composition balanced at positions 1-12. At position 13 and 14, the molecular barcodes longer than the shortest molecular barcode omit thymine to avoid signal oversaturation due to the constant 3'-overhang thymine nucleotide.

Laser-colored balancing and base-composition balancing at any given position of the molecular barcode amongst the plurality of sequence adapters is preferably measured against the length of the shortest molecular barcode. This is because, in some embodiments, a constant 3'-overhang is adjacent to the molecular barcode in the sequencing adapter, which can cause a strong signal for that particular nucleotide. Including the same nucleotide at the position of a longer molecular barcode that overlaps the 3'-overhang following a shorter barcode, would add to the signal of the nucleotide in the 3'-overhang. Thus, in some embodiments, the molecular barcodes do not include the nucleotide present in the 3'-overhang at any position that would be co-sequenced with the 3'-overhang. FIG. 3 presents a heatmap of 96 molecular barcodes of 12, 13, or 14 nucleotides long, wherein each molecular barcode is followed by a 3'-overhang thymine (T). The shortest molecular barcodes are 12 nucleotides in length. Thus, all 96 molecular barcodes are base-composition balanced through the first 12 nucleotides. At position 13, sequencing adapters with the shortest (12 nucleotide) molecular barcodes will exhibit a signal for the 3'-overhang (T). To avoid an overwhelming T signal, molecular barcodes 13 or 14 nucleotides in length do not have a thymine at position 13. Similarly, at position 14, molecular barcodes 13 nucleotides in length with exhibit a signal for the constant 3'-overhang (T). Thus, to avoid an overwhelming T signal, molecular barcodes 14 nucleotides in length do not have a thymine at position 14.

Figure 4:
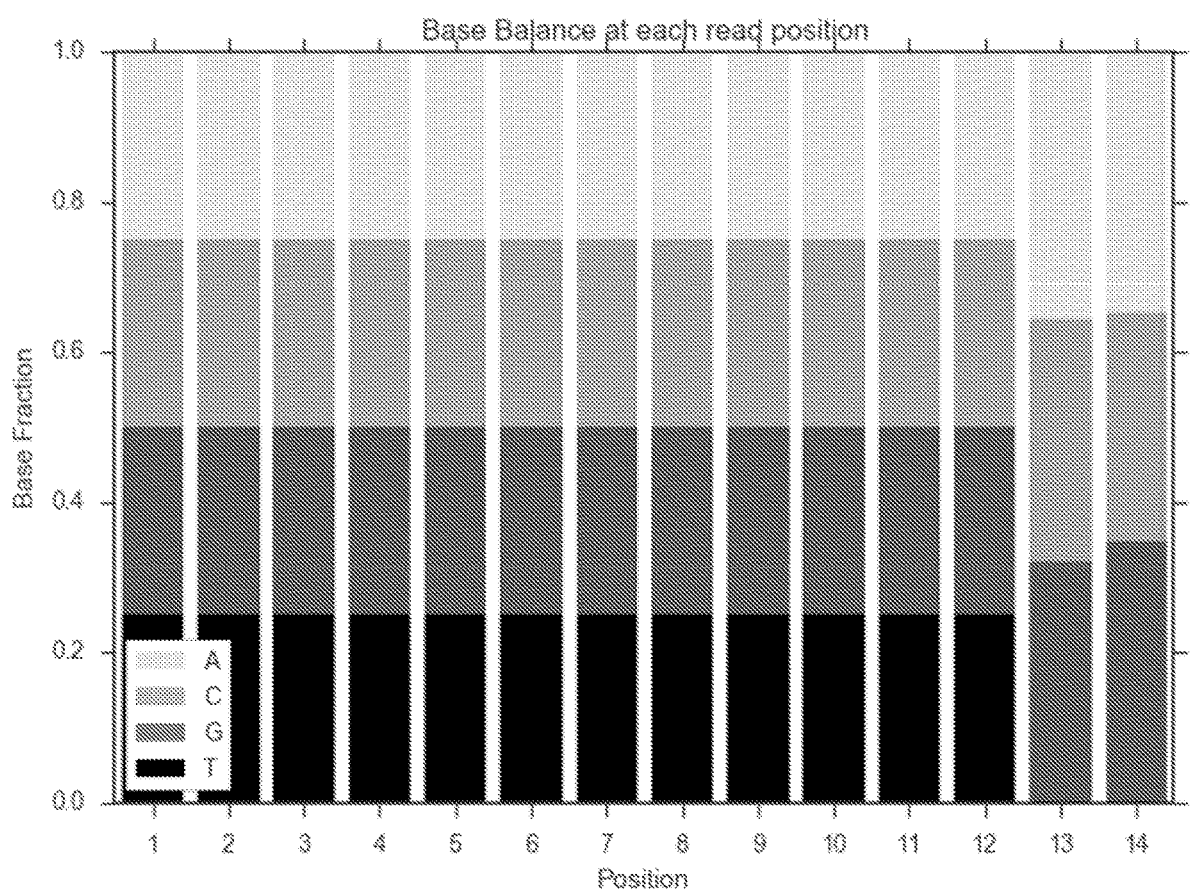
FIG. 4 provides one example of 96 base-composition balanced molecular barcodes of 12, 13, or 14 nucleotides in length, with a constant 3'-overhang thymine nucleotide adjacent to the molecular barcode. Due to the constant 3'-overhang thymine following each of the molecular barcodes, thymine is omitted at positions 13 and 14.

In some embodiments, the proportion of any given nucleotide (e.g., A, T, C, or G) at any given position of the molecular barcode amongst the plurality of sequence adapters is between about 0.2 and about 0.3 (such as about 0.25) at the corresponding position relative to the shortest molecular barcode in the plurality of sequencing adapters, and between about 0.25 and about 0.4 (such as about 0.33) for any given nucleotide other than the constant 3'-overhang nucleotide at any position beyond the length of the shortest molecular barcode. FIG. 4 provides one example of 96 base-composition balanced molecular barcodes of 12, 13, or 14 nucleotides in length, with a constant 3'-overhang thymine nucleotide adjacent to the molecular barcode (i.e., at the 13th position for a molecular barcode of 12 nucleotides in length, at the 14th position for a molecular barcode of 13 nucleotides in length, and at the 15th position for a molecular barcode 14 nucleotides in length). As can be seen in FIG. 4, the proportion (i.e., base fraction) for each of T, G, C, and A is about 0.25 for each of positions 1-12. Starting at position 13, a thymine nucleotide signal is given for each nucleic acid molecule having a molecular barcode 12 nucleotides in length. Thus, thymine is omitted for the longer molecular barcodes, and the proportion for each of G, C, and A is about 0.33 for each of position 13 or 14.

Figure 5:
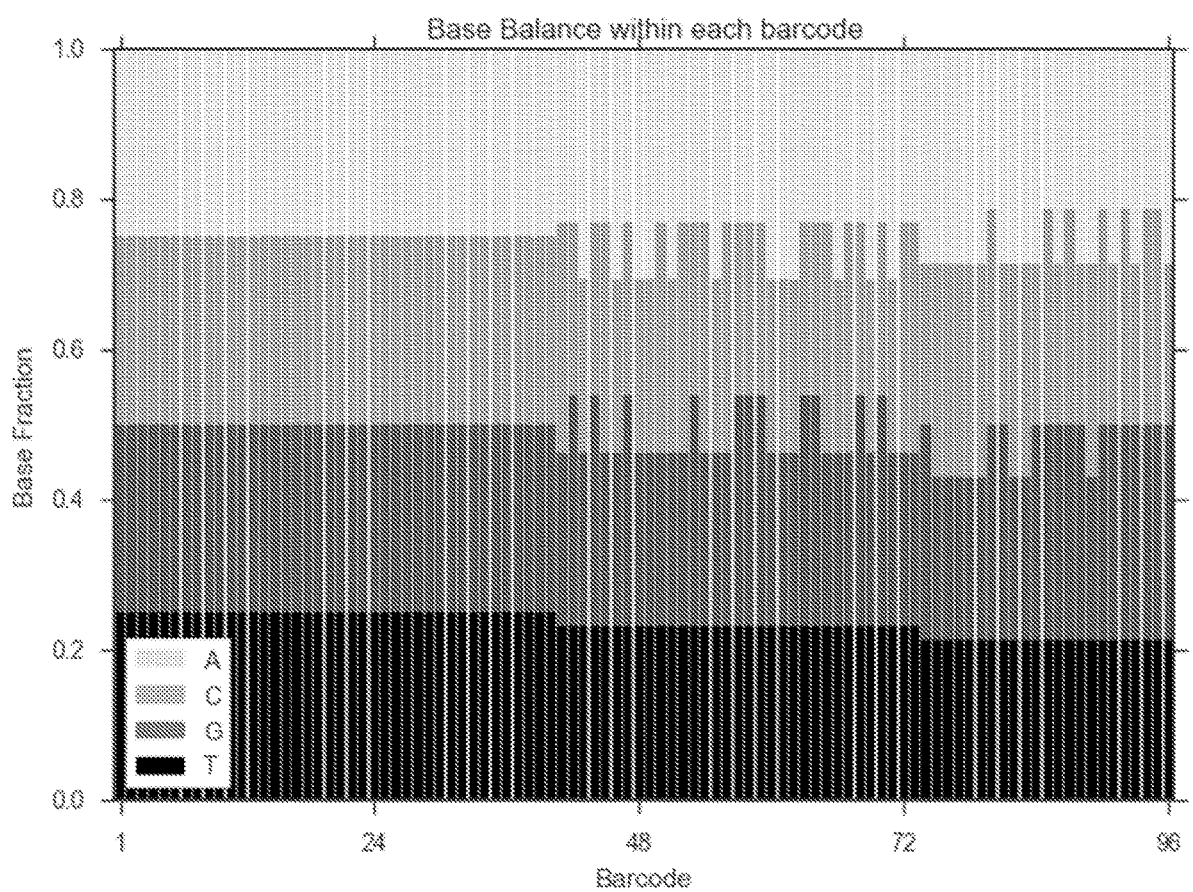
FIG. 5 illustrates the base fraction within a given molecular barcode for an exemplary set of 96 molecular barcodes.

Laser-color balancing and base-composition balancing within any given molecular barcode can be determined by counting the fraction of different nucleotide types within any molecular barcode. Base-composition balance need not be precisely balanced. For example, in molecular barcodes with a length not divisible by 4, an imperfect balance is inevitable. FIG. 5 illustrates the base fraction within a given molecular barcode for an exemplary set of 96 molecular barcodes.

In some embodiments, the molecular barcodes include additional engineering features to enhance the sequencing quality. For example, in some embodiments, the molecular barcodes do not include homopolymer sequences (such as three or more consecutive, identical nucleotides; three or more consecutive, identical nucleotides; four or more consecutive, identical nucleotides; five or more consecutive, identical nucleotides; or six or more consecutive, identical nucleotides). In some embodiments, the molecular barcodes are non-self-complementary (i.e., a single strand of the molecular barcode is not complementary to itself, for example a hairpin structure).

Preparation of Nucleic Acids for Sequencing

Methods are provided herein for preparing target nucleic acid duplex molecules for sequencing. A nonlimiting, exemplary illustration of the method is depicted in FIG. 8. In some embodiments, a library that contains a plurality of nucleic acid duplexes is prepared according to the methods described herein.

In one embodiment, the method includes:

(a) ligating an adaptor to each end of a target nucleic acid duplex, wherein the nucleic acid duplex includes first and second nucleic acid strands that are complementary to one another, wherein each of said adaptors includes: (i) a double stranded region that includes a molecular barcode; and (ii) first and second single stranded regions, wherein the first single stranded region and optionally, a portion of the double stranded region, of each of said adaptors includes a sequence S1 that is 5' of the molecular barcode sequence and the second single stranded region and optionally, a portion of the double stranded region, of each adaptor includes sequence S2' that is 3' of the molecular barcode sequence, wherein sequences S1 and S2' are different;

(b) amplifying the ligated nucleic acids produced in (a) using primers with sequence S1 and the complement of sequence S2', thereby producing (i) amplified copies of the first strand that include sequence S1 at the 5' end and a first molecular barcode A between S1 and the target nucleic acid sequence of the first strand, and sequence S2' at the 3' end and a second molecular barcode B between S2' and the target nucleic acid sequence of the first strand; (ii) amplified copies of the second strand that include sequence S1 at the 5' end and the complement B' of the second molecular barcode sequence between S1 and the target nucleic acid sequence of the second strand, and sequence S2' at the 3' end and the complement A' of the first molecular barcode sequence between S2' and the target nucleic acid sequence of the second strand; and amplified complements of (i) and (ii);

(c) hybridizing and extending a primer that includes: (i) a probe sequence that is complementary to a portion of the target nucleic acid sequence of the first and/or second strand, and (ii) a sequence S3, thereby producing primer extension products complementary to the second strand that include S3 at the 5' end and either S1' or S2' at the 3' end and that include molecular barcode sequence B between the target nucleic acid sequence and S1' or S2', and/or primer extension products complementary to the first strand that include S3 at the 5' end and either S1' or S2' at the 3' end and that include molecular barcode sequence A' between the target nucleic acid sequence and S1' or S2'; and (d) differentially amplifying the primer extension products, for example, but not limited to, in reactions that are temporally or spatially separated, wherein a first reaction includes amplification using a first primer that includes a sequence complementary to S3 and optionally, one or more sample index sequence(s), and a second primer that includes S2 and optionally, one or more sample index sequence(s), and wherein a second reaction includes amplification using a first primer that includes a sequence complementary to S3 and optionally, one or more sample index sequence(s), and a second primer that includes S1 and optionally, one or more sample index sequence(s), thereby producing amplified primer extension products for sequencing. In one embodiment, the method further includes: (e) combining the primer extension products produced in separate amplification reactions in (d), prior to sequencing. In some embodiments, the method may initiate at any of the above steps, i.e., step (a), (b), (c), or (d).

In the methods described herein, the amplification step (e.g., step (b) as described above), allows each of the two strands of the target nucleic acid duplex to be represented as both that strand and its complement, shown in FIG. 8 as plus ("+") and minus ("−") strands. The first and second strands of the target nucleic acid duplex are independently amplified with primers that are specific to the sequencing adaptors, thereby creating a sample library in which the first strand and the second strand are each represented as both a plus strand and a minus strand.

In one embodiment, the method includes:

(a) amplifying a target nucleic acid duplex that includes an adaptor ligated to each end, wherein the nucleic acid duplex includes first and second nucleic acid strands that are complementary to one another, wherein each of said adaptors includes: (i) a double stranded region that includes a molecular barcode; and (ii) first and second single stranded regions, wherein the first single stranded region and optionally, a portion of the double stranded region, of each of said adaptors includes a sequence S1 that is 5' of the molecular barcode sequence and the second single stranded region and optionally, a portion of the double stranded region, of each adaptor includes sequence S2' that is 3' of the molecular barcode sequence, wherein sequences S1 and S2' are different, wherein said amplifying includes using primers with sequence complementarity to S1 and S2', thereby producing (i) amplified copies of the first strand that include sequence S1 at the 5' end and a first molecular barcode A between S1 and the target nucleic acid sequence of the first strand, and sequence S2' at the 3' end and a second molecular barcode B between S2' and the target nucleic acid sequence of the first strand; (ii) amplified copies of the second strand that include sequence S1 at the 5' end and the complement B' of the second molecular barcode sequence between S1 and the target nucleic acid sequence of the second strand, and sequence S2' at the 3' end and the complement A' of the first molecular barcode sequence between S2' and the target nucleic acid sequence of the second strand; and amplified complements of (i) and (ii);

(b) hybridizing and extending a primer that includes: (i) a probe sequence that is complementary to a portion of the target nucleic acid sequence of the first and/or second strand, and (ii) a sequence S3, thereby producing primer extension products complementary to the second strand that include S3 at the 5' end and either S1' or S2' at the 3' end and that include molecular barcode sequence B between the target nucleic acid sequence and S1' or S2', and/or primer extension products complementary to the first strand that include S3 at the 5' end and either S1' or S2' at the 3' end and that include molecular barcode sequence A' between the target nucleic acid sequence and S1' or S2'; and (c) differentially amplifying the primer extension products, for example, but not limited to, in reactions that are temporally or spatially separated, wherein a first reaction includes amplification using a first primer that includes a sequence complementary to S3 and optionally, one or more sample index sequence(s), and a second primer that includes S2 and optionally, one or more sample index sequence(s), and wherein a second reaction includes amplification using a first primer that includes a sequence complementary to S3 and optionally, one or more sample index sequence(s), and a second primer that includes S1 and optionally, one or more sample index sequence(s), thereby producing amplified primer extension products for sequencing. In one embodiment, the method further includes: (d) combining the primer extension products produced in separate amplification reactions in (c), prior to sequencing.

In one embodiment, the method includes:

(a) hybridizing and extending a primer that includes: (i) a probe sequence that is complementary to a portion of a first and/or second strand of a target duplex nucleic acid sequence, and (ii) a sequence S3, thereby producing primer extension products complementary to the second strand that include S3 at the 5' end and either S1' or S2' at the 3' end and that include molecular barcode sequence B between the target nucleic acid sequence and S1' or S2', and/or primer extension products complementary to the first strand that include S3 at the 5' end and either S1' or S2' at the 3' end and that include molecular barcode sequence A' between the target nucleic acid sequence and S1' or S2', wherein each end of the target nucleic acid duplex is ligated to an adaptor, wherein the nucleic acid duplex includes first and second nucleic acid strands that are complementary to one another, wherein each of said adaptors includes: (i) a double stranded region that includes a molecular barcode; and (ii) first and second single stranded regions, wherein the first single stranded region and optionally, a portion of the double stranded region of each of said adaptors, includes a sequence S1 that is 5' of the molecular barcode sequence and the second single stranded region and optionally, a portion of the double stranded region of each adaptor, includes sequence S2' that is 3' of the molecular barcode sequence, wherein sequences S1 and S2' are different, wherein the ligated nucleic acid duplex is amplified by using primers with sequence complementarity to S1 and S2', thereby producing (i) amplified copies of the first strand that include sequence S1 at the 5' end and a first molecular barcode A between S1 and the target nucleic acid sequence of the first strand, and sequence S2' at the 3' end and a second molecular barcode B between S2' and the target nucleic acid sequence of the first strand; (ii) amplified copies of the second strand that include sequence S1 at the 5' end and the complement B' of the second molecular barcode sequence between S1 and the target nucleic acid sequence of the second strand, and sequence S2' at the 3' end and the complement A' of the first molecular barcode sequence between S2' and the target nucleic acid sequence of the second strand; and amplified complements of (i) and (ii); and (b) differentially amplifying the primer extension products, for example, but not limited to, in reactions that are temporally or spatially separated, wherein a first reaction includes amplification using a first primer that includes a sequence complementary to S3 and optionally, one or more sample index sequence(s), and a second primer that includes S2 and optionally, one or more sample index sequence(s), and wherein a second reaction includes amplification using a first primer that includes a sequence complementary to S3 and optionally, one or more sample index sequence(s), and a second primer that includes S1 and optionally, one or more sample index sequence(s), thereby producing amplified primer extension products for sequencing. In one embodiment, the method further includes: (c) combining the primer extension products produced in separate amplification reactions in (b), prior to sequencing.

In one embodiment, the method includes: differentially amplifying primer extension products, for example, but not limited to, in reactions that are temporally or spatially separated, wherein a first reaction includes amplification using a first primer that includes a sequence complementary to S3 and optionally, one or more sample index sequence(s), and a second primer that includes S2 and optionally, one or more sample index sequence(s), and wherein a second reaction includes amplification using a first primer that includes a sequence complementary to S3 and optionally, one or more sample index sequence(s), and a second primer that includes S1 and optionally, one or more sample index sequence(s), thereby producing amplified primer extension products for sequencing, wherein the primer extension products are prepared by a method that includes: (a) ligating an adaptor to each end of a target nucleic acid duplex, wherein the nucleic acid duplex includes first and second nucleic acid strands that are complementary to one another, wherein each of said adaptors includes: (i) a double stranded region that includes a molecular barcode; and (ii) first and second single stranded regions, wherein the first single stranded region and optionally, a portion of the double stranded region, of each of said adaptors includes a sequence S1 that is 5' of the molecular barcode sequence and the second single stranded region and a optionally, portion of the double stranded region, of each adaptor includes sequence S2' that is 3' of the molecular barcode sequence, wherein sequences S1 and S2' are different; (b) amplifying the ligated nucleic acids produced in (a) using primers with sequence S1 and the complement of sequence S2', thereby producing (i) amplified copies of the first strand that include sequence S1 at the 5' end and a first molecular barcode A between S1 and the target nucleic acid sequence of the first strand, and sequence S2' at the 3' end and a second molecular barcode B between S2' and the target nucleic acid sequence of the first strand; (ii) amplified copies of the second strand that include sequence S1 at the 5' end and the complement B' of the second molecular barcode sequence between S1 and the target nucleic acid sequence of the second strand, and sequence S2' at the 3' end and the complement A' of the first molecular barcode sequence between S2' and the target nucleic acid sequence of the second strand; and amplified complements of (i) and (ii); and (c) hybridizing and extending a primer that includes: (i) a probe sequence that is complementary to a portion of the target nucleic acid sequence of the first and/or second strand, and (ii) a sequence S3, thereby producing primer extension products complementary to the second strand that include S3 at the 5' end and either S1' or S2' at the 3' end and that include molecular barcode sequence B between the target nucleic acid sequence and S1' or S2', and/or primer extension products complementary to the first strand that include S3 at the 5' end and either S1' or S2' at the 3' end and that include molecular barcode sequence A' between the target nucleic acid sequence and S1' or S2'. In one embodiment, the method further includes: combining the primer extension products produced in the separate amplification reactions, prior to sequencing.

In a nonlimiting embodiment, the primer that includes a probe sequence that is complementary to a portion of the target nucleic acid sequence includes sequence S3 comprising or consisting of the polynucleotide sequence depicted in SEQ ID NO:5.

In some embodiments, the step of hybridizing and extending the primer that includes a probe sequence that is complementary to a portion of the target nucleic acid sequence and includes sequence S3 includes inclusion of blocking oligonucleotides that include sequences S1 and S2, and that each include a modification at the 3' end to prevent extension by a polymerase. In some embodiments, the modification at the 3' end includes 3' Spacer C3, 3' phosphate, 3' dideoxynucleoside (e.g., ddc, ddA, ddG, ddU, ddI, etc.), or 3' inverted dT.

In nonlimiting embodiments, the primers that are used for amplification of the primer extension products comprise or consist of the sequences depicted in SEQ ID NOs: 6 and 9, 7 and 10, and 8 and 11.

Sequencing

Methods for sequencing nucleic acids are provided. The methods include preparing a target nucleic acid duplex, or a plurality of target nucleic acid duplexes, for sequencing, employing methods described herein, and sequencing the products of the preparation methods, e.g., the amplified primer extension products of any of the preparation methods described herein.

In some embodiments, one or more first reads of a first strand of the target nucleic acid is performed, by sequencing with a mixture of primers that each include a sequence that is complementary to a sequence of the adaptor or its complement that is incorporated into the primer extension products for sequencing. For example, a first strand read may be conducted with a mixture of primers that each includes the sequence S1 or S2 or with first primers that include the sequence S1 and second primers that include the sequence S2 in different reaction mixtures. In some embodiments, the DNA may be spatially separated in different lanes of a flowcell, e.g., temporal, spatial, staggered, or other type of separation.

In some embodiments, the first read with one primer begins 5' of the molecular barcode sequence, and the first read with the other primer begins at the terminus of the molecular barcode sequence or within a sequence that is 5' of the adaptor sequence or its complement, such as a sample index sequence.

In some embodiments, one or more second reads is performed to read a sequence of the primer extension product, such as a sequence that is 5' of the adaptor sequence, such as a sample index sequence.

In some embodiments, a set of first reads is compiled to construct a consensus sequence of the first strand of the target nucleic acid duplex, for example, based on sequence distance or alignment to a reference sequence. For example, a first strand consensus sequence may be constructed by: comparing first strand reads in a set of first strand reads; identifying and removing errors in the set of first strand reads; and constructing an error-corrected first strand consensus sequence. In some embodiments, one or more mutation(s) may be identified by comparison of the first strand consensus sequence, e.g., error-corrected first strand consensus sequence to a reference sequence.

In some embodiments, the second strand of the target nucleic acid duplex is sequenced and a consensus sequence of the second strand is constructed. For example, a second strand consensus sequence may be constructed by: comparing second strand reads in a set of second strand reads; identifying and removing errors in the set of second strand reads; and constructing an error-corrected second strand consensus sequence.

In some embodiments, one or more lesion(s), e.g., chemical lesion(s), may be identified by comparing first and second strand consensus sequences, e.g., error-corrected first and second strand consensus sequences. In some embodiments, a lesion, e.g., chemical lesion, and a mutation may be distinguished by comparing first and second strand consensus sequences, e.g., error-corrected first and second strand consensus sequences, for example, where an error or difference in one strand versus the other strand indicates a lesion. In some embodiments, comparing first and second strand consensus sequences includes: comparing the first strand consensus sequence and the second strand consensus sequence; identifying and removing errors in the set of first strand reads and the set of second strand reads; and constructing an error-corrected duplex consensus sequence.

Sequencing can be performed using any known sequencing method, such as single-molecule real-time sequencing, ion semiconductor sequencing, pyrosequencing, massively parallel signature sequencing, or sequencing-by-synthesis chemistry. An exemplary method of sequencing-by-synthesis chemistry is performed using an Illumina HiSeq 2500® sequencer or an Illumina HiSeq 4000® sequencer.

In some embodiments, the first strand of the target nucleic acid duplex molecule is sequenced, resulting in a set of first strand reads. In some embodiments, the first strand of the duplex nucleic acid molecule is sequenced, resulting in a set of first strand reads, and the second strand of the duplex nucleic acid molecule is sequencing, resulting in a set of second strand reads.

Once the sets of strand reads are generated, a consensus sequence can be generated using the set of strand reads. In some embodiments, the sets are compiled (that is, a strand read can be assigned to a set of strand reads). The sets can be compiled, for example, based on the similarity of the molecular barcodes in the strand reads. The similarity can be determined, for example, using a sequence distance, an alignment to a reference genome, or a combination thereof. In some embodiments, compiling the sets of strand reads on the basis of the molecular barcodes alone is insufficient, and the sequence of the nucleic acid molecule is also used to compile the sets (i.e., the full strand read). The probability that two different parent nucleic acid molecules having an identical or very high sequence identity will ligate to two identical molecular barcodes is extremely low. Thus, in some embodiments, both the sequence of the molecular barcode and the sequence of the nucleic acid molecule insert are used to compile the sets.

In some embodiments, sequence distance is used as a basis for compiling the sets of strand reads. For example, in some embodiments, sequence identity is used as a basis for compiling the sets of strand reads. Sequence identity can be used as a basis for compiling the sets of strand reads by requiring a first sequence to have a sequence identity to a second sequence above a predetermined threshold. For example, in some embodiments, the molecular barcodes must be an exact match (i.e., 100% identity), about 95% identity or higher, about 90% identity or higher, or about 85% or identity or higher to be compiled into the same set. In some embodiments, the strand reads must be about 99.9% identity or higher, about 99.8% identity or higher, about 99.5% identity or higher, about 99% identity or higher, about 95% identity or higher, or about 90% identity or higher to be compiled into the same set. In another example, edit distance can be used as a basis for compiling the sets of strand reads. For example, in some embodiments, the strand reads (or molecular barcode) must have an edit distance of 1 or less, 2 or less, 3 or less, 4 or less, 5 or less, 6 or less, 7 or less, 8 or less, 9 or less, 10 or less, 11 or less, 12 or less, 13 or less, 14 or less, or 15 or less to be compiled into the same set of strand reads. Other metrics that distinguish on the basis of sequence distance can also be used, such as Hamming distance, K-mer lookup tables, or probability models for sequencer errors. The sets can be identified using any grouping method, for example by using a cutoff threshold, clustering, hierarchical clustering, K-means clustering, or using a mixture model.

In some embodiments, alignment to a reference sequence is used to compile the sets of strand. For example, the sequence of strand read (which optionally excludes the molecular barcode), can be aligned to a known reference sequence. Based on the alignment location, the set of strand reads is compiled.

In some embodiments, a consensus sequence is constructed using the set of strand reads. In some embodiments, strand reads comprising variants are removed from the set before the consensus sequence is constructed. In some embodiments, a consensus sequence is constructed and compared to the strand reads, and strand reads that are inconsistent with the consensus sequence are removed from the set of strand reads. To sequence a nucleic acid library, a consensus sequence is constructed for each (or a subset of) the sets of strand reads.

In some embodiments, the consensus sequence is compared to the strand reads in the set of strand reads. Variants between the strand reads and the consensus sequence can be identified as errors that arose through laboratory manipulation (e.g., amplification or sequencing) or through chemical damage of the original nucleic acid molecules.

In some embodiments, a first strand consensus sequence is constructed for a first strand of a duplex nucleic acid molecule from a set of first strand reads, and a second strand consensus sequence is constructed for a second strand of the duplex nucleic acid molecule, wherein the first strand and the second strand are complementary. Chemical damage to a duplex nucleic acid molecule can result in a variant in one strand of a duplex nucleic acid molecule, but not the complementary strand of the duplex nucleic acid molecule. By comparing a consensus sequence for a nucleic acid strand to the consensus sequence for its complement, variants between the strands can be identified as chemical damage.

FIG. 6 illustrates one embodiment of a method of sequencing a duplex nucleic acid molecule. A composition comprising a plurality of sequencing adapters is combined with a duplex nucleic acid molecule. The duplex nucleic acid molecule can be in a sequencing library comprising a plurality of duplex nucleic acid molecules. The sequencing adapters include the molecular barcode (marked by letters (A, B, C, etc.) to denote different sequences). The duplex nucleic acid molecule include a first strand (Strand 1, solid line) and a second strand (Strand 1', dashed line). As illustrated, the duplex nucleic acid molecule is in a sequencing library with a plurality of duplex nucleic acid molecules with a first strand (e.g., Strand 1, Strand 2, Strand 3, etc.) and a complementary second strand (e.g., Strand 1', Strand 2', Strand 3', etc.). The sequencing adapters are randomly ligated to the duplex nucleic acid. In the illustrated example, a sequencing adapter with a molecular barcode labeled "A" and "B" are ligated to the duplex nucleic acid with Strand 1 and Strand 1'. The duplex nucleic acid is then amplified to produce multiple copies of the duplex nucleic acid. Solely by way of example, a single-base mutation was introduced into the second set of strands Strand 1' during amplification (noted by a back circle). During amplification, the error is propagated. Thus, amplification yields Strand 1 and its complement, and Strand 1' and its complement (including errors that were incorporated during amplification). After amplification and application of a method disclosed herein for preparation of the target duplex for sequencing, the first strand (or both the first strand and the second strand) is sequenced, thereby generating a set of sequencing reads. A consensus sequence from the reads can then be generated using the set of Strand 1 reads, as shown in FIG. 7A.

Figure 7A:
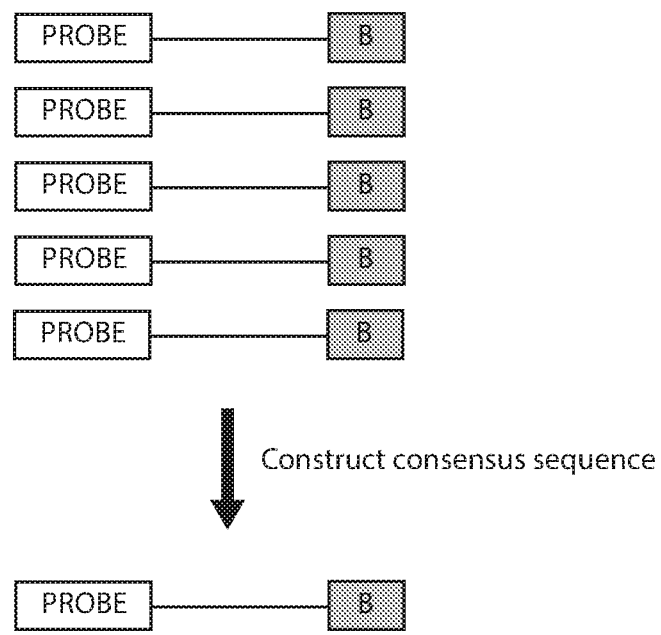
FIG. 7A illustrates an exemplary construction of a consensus sequence with a set of first strand reads from a duplex nucleic acid. Each strand read includes identical molecular barcodes, as each read arose from the same parent nucleic acid molecule.

Referring now to FIG. 7A, a consensus sequence is generated using the set of strand reads illustrated in FIG. 6. The molecular barcodes are identified, and the set of strand reads is compiled based on identity between the molecular barcodes, and a consensus sequence is constructed. Since the mutation occurs in the minority of strand reads, it is removed from the consensus sequence. Optionally, the consensus sequence is then compared to the set of strand reads, and variant strand reads are removed. Also optionally, an error-corrected consensus sequence can be constructed using the set of strand reads with the variant strand reads removed.

Referring now to FIG. 7B, a set of first strand (Strand 1) reads and a set of second strand (Strand 1') reads are generated by sequencing both the first strand and the second strand, as generated using the process shown in FIG. 6. Solely by way of example, an error arose in Strand 1' during amplification, which was further propagated in both Strand 1' and its complement. Thus, when the consensus sequence for Strand 1' is constructed, it is not possible to determine the correct sequence at that location (indicated by the black dot surrounded by parenthesis). However, because there is variance in the sets of reads, it is possible to identify the location of an error. The consensus sequence from the set of first strand (Strand 1) reads can be compared to the consensus sequence from the set of second strand (Strand 1') reads or to the second strand reads in the set of second strand (Strand 1') reads to identify the error. The consensus sequence can also be compared to a reference sequence to identify the error. Optionally, consensus sequence can be aligned with a reference sequence to identify the error. Once the error is removed, an error corrected consensus sequence can be constructed, thereby generating an error corrected consensus sequence for the duplex nucleic acid.

In FIG. 7C, Strand 1 includes an error at a base that arose prior to amplification, for example a chemical error in the parent nucleic acid molecule. Thus, the error was propagated when the nucleic acid molecule was amplified and sequenced. Thus all of the Strand 1' reads include this error. The complement strand, Strand 1, did not have this chemical error, and thus the base was correct when the parent nucleic acid molecule was amplified and the amplicons sequenced. Thus, the consensus sequence for Strand 1' includes the error, whereas the consensus sequence for Strand 1 does not include the error. If the error was a true variant in the original duplex nucleic acid, then both Strand 1 and Strand 1' would include the variant. Comparing the consensus sequence for Strand 1 with the consensus sequence for Strand 1' allows for identification of an error at that position, as only one of the consensus sequences include the error. The consensus sequences can be compared to a reference sequence to determine whether the consensus sequence for Strand 1 or the consensus sequence for Strand 1' gives the correct sequence.

Although the foregoing invention has been described in some detail by way of illustration and examples for purposes of clarity of understanding, it will be apparent to those skilled in the art that certain changes and modifications may be practiced without departing from the spirit and scope of the invention. Therefore, the description should not be construed as limiting the scope of the invention.

All publications, patents, and patent applications cited herein are hereby incorporated by reference in their entireties for all purposes and to the same extent as if each individual publication, patent, or patent application were specifically and individually indicated to be so incorporated by reference.

---

Nucleotide Sequences

SEQ ID NO: 1 <barcode sequence A> CATCGAGCTATGAT

SEQ ID NO: 2 <barcode sequence B> ACACGCTACGATGT

SEQ ID NO: 3 <S1> CACTCAGCAGCACGACGATCACAGATGTGTATAAGAGACAGT

Nucleotide Sequences

SEQ ID NO: 4 <S2'> ACTGTGTAAAACGACGGCCAGT

SEQ ID NO: 5 <probe with sequence S3> CAGACGTGTGCTCTTCCGATCT

SEQ ID NOs: 6 and 9 <primer P7/SI7/S3>
CAAGCAGAAGACGGCATACGAGAT[index_i7]GTGACTGGAGTTCAGACGTGTGCTC
TTCCGATCT SEQ ID NOs: 7 and 10 <primer P5/SI5'/S2>
AATGATACGGCGACCACCGAGATCTACAC[index_i5]TAATACGACTCACTATAGGG
ACTGGCCGTCGTTTTACACAGT SEQ ID NOs: 8 and 11 <primer P5/SI5/S1>
AATGATACGGCGACCACCGAGATCTACAC[index_i5]CACTCAGCAGCACGACGATC
ACAGATGTGTATAAGAGACAGT

We claim:

1. A method for preparing a target nucleic acid duplex molecule for sequencing, comprising:
   (a) ligating an adaptor to each end of a target nucleic acid duplex,
       wherein the nucleic acid duplex comprises first and second nucleic acid strands that are complementary to one another,
       wherein each of said adaptors comprises: (i) a double stranded region that comprises a molecular barcode; and (ii) first and second single stranded regions,
       wherein the first single stranded region and optionally, a portion of the double stranded region, of each of said adaptors comprises a sequence S1 that is 5' of the molecular barcode sequence and the second single stranded region and optionally, a portion of the double stranded region, of each adaptor comprises sequence S2' that is 3' of the molecular barcode sequence, wherein sequences S1 and S2' are different;
   (b) amplifying the ligated nucleic acids produced in (a) using primers with sequence S1 and the complement of S2', thereby producing (i) amplified copies of the first strand that comprise sequence S1 at the 5' end and a first molecular barcode A between S1 and the target nucleic acid sequence of the first strand, and sequence S2' at the 3' end and a second molecular barcode B between S2' and the target nucleic acid sequence of the first strand; (ii) amplified copies of the second strand that comprise sequence S1 at the 5' end and the complement B' of the second molecular barcode sequence between S1 and the target nucleic acid sequence of the second strand, and sequence S2' at the 3' end and the complement A' of the first molecular barcode sequence between S2' and the target nucleic acid sequence of the second strand; and amplified complements of (i) and (ii);
   (c) hybridizing and extending a primer that comprises: (i) a probe sequence that is complementary to a portion of the target nucleic acid sequence of the first and/or second strand, and (ii) a sequence S3, thereby producing primer extension products complementary to the second strand that comprise S3 at the 5' end and either S1' or S2' at the 3' end and that comprise molecular barcode sequence B between the target nucleic acid sequence and S1' or S2', and/or primer extension products complementary to the first strand that comprise S3 at the 5' end and either S1' or S2' at the 3' end and that comprise molecular barcode sequence A' between the target nucleic acid sequence and Si' or S2';
   (d) differentially amplifying the primer extension products,
       wherein a first reaction comprises amplification using a first primer that comprises a sequence complementary to S3 and optionally, one or more sample index sequence(s), and a second primer that comprises S2 and optionally, one or more sample index sequence(s), and
       wherein a second reaction comprises amplification using a first primer that comprises a sequence complementary to S3 and optionally, one or more sample index sequence(s), and a second primer that comprises S1 and optionally, one or more sample index sequence(s),
       thereby producing amplified primer extension products for sequencing.

2. The method according to claim 1, wherein the adaptors are Y-shaped with first and second single stranded regions on separate polynucleotides.

3. The method according to claim 1, wherein the adaptors are U-shaped with first and second single stranded regions on the same polynucleotide.

4. The method according to claim 1, wherein step (c) comprises inclusion of blocking oligonucleotides that comprise sequences S1 and S2, and that each comprise a modification at the 3' end to prevent extension by a polymerase.

5. The method according to claim 1, wherein the molecular barcode sequences are 4-15 nucleotides in length.

6. The method according to claim 1, further comprising:
   (e) combining the primer extension products produced in separate amplification reactions in (d), prior to sequencing.

7. The method according to claim 1, wherein barcode sequences A and B are different.

8. The method according to claim 1, wherein barcode sequences A and B are the same.

9. The method according to claim 1, wherein the sample index sequence(s), if any, on the first primer are different from the sample index sequence(s) on the second primer in step (d).

10. The method according to claim 1, wherein the sample index sequence(s), if any, on the first primer are the same as the sample index sequence(s) on the second primer in step (d).

11. The method according to claim 1, wherein said amplifying in step (b) comprises polymerase chain reaction (PCR) or a linear amplification method.

12. The method according to claim 1, wherein said differentially amplifying in step (d) comprises temporal or spatial separation of said first and second reactions.

13. The method according to claim 1, wherein said amplifying in step (d) comprises PCR or a linear amplification method.

14. The method according to claim 1, comprising performing step (c) with a plurality of different probes, in the same or different reaction mixtures, to produce a plurality of primer extension products that will provide different start points for sequencing of the target nucleic acid sequence.

15. The method according to claim 1, wherein the target nucleic acid duplex comprises cell-free DNA.

16. The method according to claim 15, wherein the cell-free DNA comprises cell-free tumor DNA or cell-free fetal DNA.

17. The method according to claim 1, wherein the target nucleic acid duplex is enriched from a nucleic acid library.

18. The method according to claim 17, wherein the target nucleic acid duplex is enriched using a set of capture probes for a region of interest.

19. The method according to claim 1, wherein the double stranded region of the adaptor comprises a sample index sequence.

20. The method according to claim 19, wherein the sample index sequence is adjacent to the molecular barcode sequence.

21. The method according to claim 20, wherein the sample index is 3' of S1 and is 5' or 3' of the molecular barcode sequence, and/or wherein the sample index is 5' of S2' and is 5' or 3' of the molecular barcode sequence.

22. The method according to claim 19, wherein the sample index is 3' of S1 and is 5' or 3' of the molecular barcode sequence, and/or wherein the sample index is 5' of S2' and is 5' or 3' of the molecular barcode sequence.

23. A method for sequencing a target nucleic acid, comprising preparing a target nucleic acid duplex for sequencing according to claim 1, and sequencing the products of step (d).

24. The method according to claim 23, comprising performing a first read of a first strand of the target sequence, comprising sequencing with first primers that comprise sequence S1 and second primers that comprise sequence S2, in the same or different reaction mixtures.

25. The method according to claim 24, wherein the first read with one of the primers begins 5' of the molecular barcode sequence and the first read with the other primer begins at the molecular barcode sequence.

26. The method according to claim 24, wherein the first read with both of the primers begins 5' of the molecular barcode sequence.

27. The method according to claim 24, wherein the first read begins at the terminus or within a sample index sequence.

28. The method according to claim 24, comprising performing second reads to read sample index sequence(s).

29. The method according to claim 24, comprising compiling a set of first reads to construct a consensus sequence of the first strand of the target nucleic acid duplex.

30. The method according to claim 29, wherein the set of first strand reads is compiled based on sequence distance or alignment to a reference sequence.

31. The method according to claim 29, wherein constructing the first strand consensus sequence comprises:
comparing the first strand reads in the set of first strand reads;
identifying and removing errors in the set of first strand reads; and
constructing an error-corrected first strand consensus sequence.

32. The method according to claim 31, comprising identifying a mutation by comparison of the error-corrected consensus sequence to a reference sequence.

33. The method according to claim 29, further comprising sequencing the second strand of the target nucleic acid duplex and constructing a consensus sequence of the second strand of the target nucleic acid duplex.

34. The method according to claim 33, further comprising:
comparing the first strand consensus sequence and the second strand consensus sequence;
identifying and removing errors in the set of first strand reads and the set of second strand reads; and
constructing an error-corrected duplex consensus sequence.

35. The method according to claim 34, comprising identifying a chemical lesion by comparison of the sequences of the two strands in the error-corrected duplex consensus sequence.

36. The method according to claim 34, comprising distinguishing between (i) a chemical lesion or introduced sequence error, and (ii) a mutation, by comparison of the sequences of the two strands in the error-corrected duplex consensus sequence, wherein an error present in one strand indicates a chemical lesion or introduced sequence error, and an error present on both strands indicates a mutation.

37. A method for sequencing a target nucleic acid, comprising preparing a target nucleic acid duplex for sequencing according to claim 6, and sequencing the products of step (e).

38. The method according to claim 37, comprising performing a first read of a first strand of the target sequence, comprising sequencing with first primers that comprise sequence S1 and second primers that comprise sequence S2, in the same or different reaction mixtures.

39. A method for preparing a nucleic acid sequencing library, comprising preparing a plurality of target DNA duplexes for sequencing in a method according to claim 1.

* * * * *